United States Patent
Yee et al.

(10) Patent No.: US 10,350,223 B2
(45) Date of Patent: Jul. 16, 2019

(54) COMPOSITIONS AND METHODS FOR TREATING OCULAR DISEASES

(71) Applicants: Richard W. Yee, Houston, TX (US); Kenneth Hughes, Houston, TX (US)

(72) Inventors: Richard W. Yee, Houston, TX (US); Kenneth Hughes, Houston, TX (US)

(*) Notice: Subject to any disclaimer, the term of this patent is extended or adjusted under 35 U.S.C. 154(b) by 0 days.

(21) Appl. No.: 15/555,527

(22) PCT Filed: Mar. 3, 2016

(86) PCT No.: PCT/US2016/020683
§ 371 (c)(1),
(2) Date: Sep. 4, 2017

(87) PCT Pub. No.: WO2016/141182
PCT Pub. Date: Sep. 9, 2016

(65) Prior Publication Data
US 2018/0050049 A1    Feb. 22, 2018

Related U.S. Application Data

(60) Provisional application No. 62/127,362, filed on Mar. 3, 2015.

(51) Int. Cl.
| | |
|---|---|
| *A61K 9/00* | (2006.01) |
| *A61K 45/06* | (2006.01) |
| *A61K 47/10* | (2017.01) |
| *A61K 47/38* | (2006.01) |
| *A61K 31/136* | (2006.01) |
| *A61K 31/145* | (2006.01) |
| *A61K 31/585* | (2006.01) |

(52) U.S. Cl.
CPC .......... *A61K 31/585* (2013.01); *A61K 9/0048* (2013.01); *A61K 31/136* (2013.01); *A61K 31/145* (2013.01); *A61K 45/06* (2013.01); *A61K 47/10* (2013.01); *A61K 47/38* (2013.01)

(58) Field of Classification Search
None
See application file for complete search history.

(56) References Cited

U.S. PATENT DOCUMENTS

| | | |
|---|---|---|
| 3,551,554 A | 12/1970 | Herschler |
| 3,711,602 A | 1/1973 | Herschler |
| 4,192,802 A | 3/1980 | Anner et al. |
| 4,543,351 A | 9/1985 | Messina |
| RE32,112 E | 4/1986 | Shapiro |
| 5,427,778 A | 6/1995 | Finkenaur et al. |
| 7,879,910 B1 | 2/2011 | Marini |
| 8,003,690 B2 | 8/2011 | Vergnault et al. |
| 8,709,393 B2 | 4/2014 | McAnulty et al. |
| 8,957,052 B2 | 2/2015 | Behar-Cohen et al. |
| 9,241,944 B2 | 1/2016 | Farman et al. |
| 9,610,294 B2 | 4/2017 | Behar-Cohen et al. |
| 9,682,089 B2 | 6/2017 | Farman et al. |
| 9,730,948 B2 | 8/2017 | Farman et al. |
| 2001/0019721 A1 | 9/2001 | Brandt et al. |
| 2003/0199483 A1 | 10/2003 | McMahon et al. |
| 2004/0043026 A1 | 3/2004 | Tuan et al. |
| 2004/0067916 A1 | 4/2004 | Delyani et al. |
| 2004/0102423 A1 | 5/2004 | MacLaughlan et al. |
| 2006/0210604 A1 | 9/2006 | Dadey et al. |
| 2009/0325918 A1 | 12/2009 | Somberg et al. |
| 2010/0003354 A1 | 1/2010 | Mastrodonato |
| 2010/0029574 A1 | 2/2010 | Marini |
| 2010/0068301 A1 | 3/2010 | Hutchinson et al. |
| 2010/0130580 A1 | 5/2010 | Ousler et al. |
| 2010/0226963 A1 | 9/2010 | Cooper et al. |
| 2012/0113384 A1 | 5/2012 | Pasternak et al. |
| 2012/0252756 A1* | 10/2012 | Coffey ................. A61K 9/0048 514/57 |
| 2013/0131024 A1 | 5/2013 | Behar-Cohen et al. |
| 2013/0143850 A1 | 6/2013 | Farman et al. |

(Continued)

FOREIGN PATENT DOCUMENTS

| | | | |
|---|---|---|---|
| EP | 0028525 A2 | 5/1981 |
| EP | 0126684 A2 | 11/1984 |

(Continued)

OTHER PUBLICATIONS

A Patel, "Ocular drug delivery systems: An overview", World J Pharmacol. 2013; 2(2): 47-64.

Agbaga, M.-P., Brush, R. S., Mandal, M. N. A., Henry, K., Elliott, M. H., Anderson, R. E. Role of Stargardt-3 macular dystrophy protein (ELOVL4) in the biosynthesis of very long chain fatty acids. Proc. Nat. Acad. Sci. 105: 12843-12848, 2008.

Aldahmesh, M. A., Mohamed, J. Y., Alkuraya, H. S., Verma, I. C., Puri, R. D., Alaiya, A. A., Rizzo, W. B., Alkuraya, F. S. Recessive mutations in ELOVL4 cause ichthyosis, intellectual disability, and spastic quadriplegia. Am. J. Hum. Genet. 89: 745-750, 2011.

Anne McMahon, Hua Lu, Igor A. Butovich; A Role for ELOVL4 in the Mouse Meibomian Gland and Sebocyte Cell Biology. Invest. Ophthalmol. Vis. Sci 2014;55(5):2832-2840. doi: 10.1167/iovs.13-13335.

Arita, R., Zavala, M., & Yee, R.W., "MGD Diagnosis," Curr Opthalmol Rep, 49-57 (Jun. 4, 2014).

(Continued)

*Primary Examiner* — Brian J Davis
(74) *Attorney, Agent, or Firm* — New River Valley IP Law, PC; Michele L. Mayberry

(57) ABSTRACT

The compositions and methods disclosed herein provide for treatments of ocular disorders of the eye, such as ocular surface diseases as well as those associated with inflammation of internal cells and cell layers of the eye. The methods disclosed herein describe methods for treating ocular disorders, particularly dry eye disorders, comprising topically administering to an ocular region of a subject a composition comprising a pharmaceutically effective amount of at least one aldosterone antagonist or salt thereof and a pharmaceutically acceptable carrier. Included is a method for treating dry eye comprising topically administering to an ocular region of a subject a composition comprising spironolactone and hydroxypropyl methylcellulose; and reducing or preventing one or more symptoms or causes of dry eye.

41 Claims, 6 Drawing Sheets

(56) References Cited

U.S. PATENT DOCUMENTS

| | | | |
|---|---|---|---|
| 2015/0216879 | A1 | 8/2015 | Behar-Cohen et al. |
| 2015/0342876 | A1 | 12/2015 | Behar-Cohen et al. |
| 2016/0082020 | A1 | 3/2016 | Farman et al. |
| 2016/0136183 | A1 | 5/2016 | Farman et al. |
| 2017/0273992 | A1 | 9/2017 | Farman et al. |

FOREIGN PATENT DOCUMENTS

| | | | |
|---|---|---|---|
| EP | 0046291 B1 | 12/1985 | |
| EP | 0410348 A1 | 1/1991 | |
| EP | 0582458 A1 | 2/1994 | |
| EP | 0603405 A1 | 6/1994 | |
| EP | 0582458 B1 | 11/1995 | |
| FR | 2588755 A1 | 4/1987 | |
| WO | 0072883 A2 | 12/2000 | |
| WO | WO 2001/034132 A2 * | 5/2001 | ............ A61K 31/00 |
| WO | 2001034132 A3 | 1/2002 | |
| WO | 03049745 A1 | 6/2003 | |
| WO | 2004085458 A2 | 10/2004 | |
| WO | 2006002022 A2 | 1/2006 | |
| WO | 2006112029 A1 | 10/2006 | |
| WO | 2010038234 A1 | 4/2010 | |
| WO | 2011157798 A1 | 12/2011 | |
| WO | 2012093117 A1 | 7/2012 | |
| WO | 2013170317 A1 | 11/2013 | |
| WO | 2014202744 A1 | 12/2014 | |

OTHER PUBLICATIONS

ATCC® Primary Cell Culture Guide, 2012, American Type Culture Collection (ATCC) website: https://www.atcc.org/~/media/PDFs/Culture%20Guides/Primary_Cell_Culture_Guide.ashx.

Bahassi and Stambrook, Next-generation sequencing technologies: breaking the sound barrier of human genetics, Mutagenesis, Sep. 2014; 29(5):303-10.

Bernstein, P. S., Tammur, J., Singh, N., Hutchinson, A., Dixon, M., Pappas, C. M., Zabriskie, N. A., Zhang, K., Petrukhin, K., Leppert, M., Allikmets, R. Diverse macular dystrophy phenotype caused by a novel complex mutation in the ELOVL4 gene. Invest. Ophthal. Vis. Sci. 42: 3331-3336, 2001.

Conley, Y. P., Jakobsdottir, J., Mah, T., Weeks, D. E., Klein, R., Kuller, L., Ferrell, R. E., Gorin, M. B. CFH, ELOVL4, PLEKHA1 and LOC387715 genes and susceptibility to age-related maculopathy: AREDS and CHS cohorts and meta-analyses. Hum. Molec. Genet. 15: 3206-3218, 2006.

Corresponding European Patent Application No. 16759492.8, filed Oct. 2, 2017.

Corresponding Japanese Patent Application No. 2017/545,950, filed Aug. 28, 2017.

Corresponding PCT Application PCT/US16/020683 International Search Report and Written Opinion dated May 19, 2016, 12 pages.

Corresponding PCT Application PCT/US16/020683, filed Mar. 3, 2016.

Craig, JP, Chen Y, Turnbull PRK. Prospective Trial of Intense Pulsed Light for the Treatment of Meibomian Gland Dysfunction. Investigative Opthalmology& Visual Sciences. 2015; 56(3):1965-70.

E. Knop et al., "The International Workshop on Meibomian Gland Dysfunction: Report of the Subcommittee on Anatomy, Physiology, and Pathophysiology of the Meibomian Gland", Invest Ophthalmol Vis Sci. Mar. 2011; 52(4): 1938-1978.

Janell R. Johnson et al..; ARVO 2017 Annual Meeting Abstracts; "Topical spironolactone in the treatment of meibomian gland dysfunction"; May 8, 2017; p. 7.

JérômeFagart, Alexander Hillisch, Jessica Huyet, Lars Bärfacker, Michel Fay, Ulrich Pleiss, Elisabeth Pook, Stefan Schäfer, Marie-Edith Rafestin-Oblin, and Peter Kolkhof A New Mode of Mineralocorticoid Receptor Antagonism by a Potent and Selective Nonsteroidal Molecule J. Biol. Chem. 2010 285: 29932-29940. First Published on Jul. 22, 2010, doi:10.1074/jbc.M110.131342.

Johnson, Janell Renee; Ali, Waju; Wong, Brian S.; Mikhail de Jesus; Yee, Richard W, Topical spironolactone in the treatment of meibomian gland dysfunction, (abstract submitted for the 2017 ARVO Annual Meeting, Baltimore, MD, May 7-11, 2017), IOVS, Jun. 2017, vol. 58, No. 8, 2249.

Kim, G.K. and Del Rosso, J.Q., "Oral Spironolactone in Postteenage Female Patients with Acne Vulgaris," J Clin Aesthet Dermatol, 5(3): 37-50 (Mar. 2012).

Maugeri, A., Meire, F., Hoyng, C. B., Vink, C., Van Regemorter, N., Karan, G., Yang, Z., Cremers, F. P. M., Zhang, K. A novel mutation in the ELOVL4 gene causes autosomal dominant Stargardt-like macular dystrophy. Invest. Ophthal. Vis. Sci. 45:4263-4267, 2004.

Murdan,"A Review of Pluronic Lecithin Organogel as a Topical and Transdermal Drug Delivery System", Hospital Pharmacist, Jul./Aug. 2005, vol. 12, pp. 267-270.

Nelson JD, Shimazaki J, Benitez-del-Castillo JM, Craig JP, McCulley JP, Den S, et al. The international workshop on meibomian gland dysfunction: report of the definition and classification subcommittee. Invest Ophthalmol Vis Sci. 2011;52(4):1930-7. doi: 10.1167/iovs.10-6997b.

Nichols et al, "The International Workshop on Meibomian Gland Dysfunction: Executive Summary", Invest. Ophthalmol. Vis. Set 52: 1922-1929, 2011.

Online Mendelian Inheritance in Man, OMIM (TM). Johns Hopkins University, Baltimore, MD. MIM No. 605512: Jan. 2, 2018: Retrieved from http://omim.org/entry/605512.

Ozaki, K., Doi, H., Mitsui, J., Sato, N., Iikuni, Y., Majima, T., Yamane, K., Irioka, T., Ishiura, H., Doi, K., Morishita, S., Higashi, M., and 11 others. A novel mutation in ELOVL4 leading to spinocerebellar ataxia (SCA) with the hot cross bun sign but lacking erythrokeratodermia: a broadened spectrum of SCA34. JAMA Neurol. 72: 797-805, 2015.

Ozlem G. Sahin, ElçinKartal, and NusretTaheri, "Meibomian Gland Dysfunction: Endocrine Aspects," ISRN Ophthalmology, vol. 2011, Article ID 465198, 6 pages, 2011. doi:10.5402/2011/465198.

Pflugfelder, "Management and Thereapy of Dry Eye Disease: Report of the Management and Thereapy Subcommittee of the International Dry Eye Workshop", The Ocular Surface 5(2): 163-178, 2007.

Qiao J, Yan X. Emerging treatment options for meibomian gland dysfunction. ClinOphthalmol. 2013;7:1797-803.

Richard W. Yee et al.; ARVO 2016 Annual Meeting Abstracts; "Topical spironolactone in the treatment of meibomian gland dysfunction"; May 5, 2016; p. 4.

Sahin, et al., "Meibomian Gland Dysfunction: Endocrine Aspects," ISRN Ophthalmology, vol. 2011, Article ID 465198, 6 pages, (2011).

Smith, "The Epidemiology of Dry Eye Disease: Report of the Epidemiology Subcommittee of the International Dry Eye Workshop", The Ocular Surface 5(2): 93-107 (2007).

Strain and Chaturvedi, "The renin-angiotensin-aldosterone system and the eye in diabetes," J Renin Angiotensin Aldosterone Syst., 3:243-246, 2002.

Strain WD, Chaturvedi N. The renin-angiotensin-aldosterone system and the eye in diabetes. J Renin Angiotensin Aldosterone Syst. 2002;3:243-246.

Tavakkoli, F., "Review of the role of Spironolactone in the therapy of children," 18th Expert Committee on the Selection and Use of Essential Medicines (Mar. 21, 2011).

Térouanne, et al., "A stable prostatic bioluminescent cell line to investigate androgen and antiandrogen effects," Molecular and Cellular Endocrinology, 160 (1-2): 39-49, (2001).

The Pharmaceutical Journal, "Topical drug dosage forms for eye conditions" Jun. 2017 online | URl: 20202915 https://www.pharmaceutical-journal.com/pharmacy-learning-centre/topical-drug-dosage-forms-for-eye-conditions/20202915.article.

TTUHSC EL Paso; "2015 SARP Symposium Winners Announced"; Jan. 4, 2016; 3 pages.

Vasireddy, V., Uchida, Y., Salem, N., Jr., Kim, S. Y., Mandal, M. N. A., Reddy, G. B., Bodepudi, R., Alderson, N. L., Brown, J. C., Hama, H., Dlugosz, A., Elias, P. M., Holleran, W. M., Ayyagari, R. Loss of functional ELOVL4 depletes very long-chain fatty acids

(56) References Cited

OTHER PUBLICATIONS (greater than C28) and the unique omega-O-acylceramides in skin leading to neonatal death. Hum. Molec. Genet. 16: 471-482, 2007.
Yee, Richard W; Wong, Brian; Mikhail Lagrimas de Jesus, Topical spironolactone in the treatment of meibomian gland dysfunction, (abstract submitted for the 2016 ARVO Annual Meeting, Seattle, Wash., May 1-5, 2016), IOVS, Sep. 2016, vol. 57, No. 12, 5664.
Zhang, K., Kniazeva, M., Han, M., Li, W., Yu, Z., Yang, Z., Li, Y., Metzker, M. L., Allikmets, R., Zack, D. J., Kakuk, L. E., Lagali, P. S., Wong, P. W., MacDonald, I. M., Sieving, P. A., Figueroa, D. J., Austin, C. P., Gould, R. J., Ayyagari, R., Petrukhin, K. A 5-bp deletion in ELOVL4 is associated with two related forms of autosomal dominant macular dystrophy. Nature Genet. 27: 89-93, 2001.
Agbaga MP, Abstract "Different Mutations in ELOVL4 Affect Very Long Chain Fatty Acid Biosynthesis to Cause Variable Neurological Disorders in Humans". Adv Exp Med Biol. 2016;854:129-35. doi: 10.1007/978-3-319-17121-0_18.
Arita et al., Abstract. "Proposed diagnostic criteria for obstructive meibomian gland dysfunction," Ophthalmology, 116:2058-2063 (2009).
Corresponding European Patent Application No. 16759492.8, Supplementary European Search Report, dated Oct. 15, 2018.
Corvol P, Michaud A, Menard J, et al. Abstract. Antiandrogenic Effect of Spirolactones: Mechanism of Action. Endocrinology 1975 97:1, 52-58.
Edwards, A. O., Miedziak, A., Vrabec, T., Verhoeven, J., Acott, T. S., Weleber, R. G., Donoso, L. A. Autosomal dominant Stargardt-like macular dystrophy: I. Clinical characterization, longitudinal follow-up, and evidence for a common ancestry in families linked to chromosome 6q14. Am. J. Ophthal. 127: 426-435, 1999.
Foulks GN, Bron AJ. Abstract. Meibomian gland dysfunction: a clinical scheme for description, diagnosis, classification, and grading. Ocul Surf. 2003;1:107-126.
Giroux, J.-M., Barbeau, A. Abstract. Erythrokeratodermia with ataxia. Arch. Derm. 106: 183-188, 1972.
Grada and Weinbrecht, Next-Generation Sequencing: Methodology and Application, Journal of Investigative Dermatology (2013) 133, e11.
Greenblatt DJ, Koch-Weser J. Abstract. Adverse Reactions to Spironolactone: A Report From the Boston Collaborative Drug Surveillance Program. JAMA. 1973;225(1):40-43. doi:10.1001/jama.1973.03220280028007.

Griesinger, I. B., Sieving, P. A., Ayyagari, R. Autosomal dominant macular atrophy at 6q14 excludes CORD7 and MCDR1/PBCRA loci. Invest. Ophthal. Vis. Sci. 41: 248-255, 2000.
Kawai, S (Abstract): "Cornea protective agent for use in ophthalmic composition for suppressing advance of corneal trauma e.g. dry eyes or corneal ulcer, contains hydroxypropyl methylcellulose", WPI/2017 Clarivate Analytics, vol. 2006, No. 76, Oct. 19, 2006 (Oct. 19, 2006), XP002764851, see also WO2006/112029.
Lagali, P. S., MacDonald, I. M., Griesinger, I. B., Chambers, M. L., Ayyagari, R., Wong, P. W. Abstract. Autosomal dominant Stargardt-like macular dystrophy segregating in a large Canadian family. Canad. J. Ophthal. 35: 315-324, 2000.
M. B. Abelson et al., "The Foundation of a Good Formulation", Review of Ophthalmology, published online Mar. 3, 2017.
Rathnayake D and Sinclair R, Abstract. Use of spironolactone in dermatology.Skinmed. Nov.-Dec. 2010;8(6):328-32; quiz 333.
Salavastru CM, Fritz K, Tiplica GS Abstract. [Spironolactone in dermatological treatment. On and off label indications.] Hautarzt. Oct. 2013;64(10):762-7. doi: 10.1007/s00105-013-2597-y.
Schein et al., "Prevalence of dry eye among the elderly," American J. Ophthalmology, 124:723-738, (1997).
Schirra F et al. Abstract. "Testosterone reduces the expression of keratinization-promoting genes in murine Meibomian glands". Ophthalmologe. Mar. 2013;110(3):230-8. doi: 10.1007/s00347-012-2661-5.
Shaw JC, White LE. Abstract. Long-term safety of spironolactone in acne: results of a 8-year followup study. J Cutan Med Surg. Nov.-Dec. 2002;6(6):541-5. Epub Sep. 12, 2002.
Sullivan, et al., Abstract. "Androgen deficiency, Meibomian gland dysfunction, and Evaporative dry eye," Ann NY Acad Sci., 966:211-222, (2002).
Tauber, J: "Efficacy, tolerability and comfort of a 0.3% hypromellose gel ophthalmic lubricant in the tratment of patients with moderate to severe dry eye syndrome", Current Medical Research and Opinion, Informa Healthcare, GB, vol. 23, No. 11, Oct. 31, 2007 (Oct. 31, 2007), pp. 2629-2636, XP009508344.
Toda, I. et al: "Hydroxypropyl methylcellulose for the treatment of severe dry eye associated with Sjogren's syndrome", Cornea: The Journal of Cornea and External Disease, Lippincott Williams & Wilkins, US, vol. 15, No. 1, Mar. 1, 1996 (Mar. 1, 1996), pp. 120-128, XP009508345.

* cited by examiner

COMPOSITIONS AND METHODS FOR TREATING OCULAR DISEASES

CROSS-REFERENCE TO RELATED APPLICATIONS

This application is a National Stage application under 35 U.S.C. § 371 of International Application No. PCT/US16/20683, filed Mar. 3, 2016, which application relies on the disclosure of and claims priority to and the benefit of the filing date of U.S. Provisional Application No. 62/127,362, filed Mar. 3, 2015, the disclosures of each of which are hereby incorporated by reference herein in their entireties.

FIELD OF THE INVENTION

Disclosed herein are compositions for treating ocular diseases. Further disclosed are methods of using such compositions for treating ocular disorders of the eye by administering the described compositions to an ocular region of a patient.

BACKGROUND OF THE INVENTION

Ocular surface diseases affect millions of Americans each year (see Schein et al., *American J. Ophthalmology*, 124: 723-738, (1997)). One such ocular surface disease, "dry eye disease", a generic description for an ocular surface disease of the tear film, can cause considerable pain and discomfort to those afflicted. Mild cases may only present symptoms of drying or irritation, while more severe cases may include burning sensations or substantial impairments to a person's vision.

Chronic dryness can adversely impact normal daily activities such as reading, driving, and engaging in outdoor activities among other things. Ocular surface diseases, such as dry eye, are on the rise, and particularly among older populations. It has been estimated that approximately 4.9 million Americans 50 years and older have dry eye or chronic dry eye disease with the number of women appearing to outnumber men similarly affected. (see Smith, *The Ocular Surface* 5(2): 93-407 (2007)).

Dry eye is typically divided into two broad classes—aqueous tear-deficient dry eye (ADDE) and evaporative dry eye (EDE). The former, ADDE, generally refers to a disorder in which the lacrimal glands fail to produce enough of the watery component of tears to maintain a healthy eye surface. ADDE can be further divided in to two major subclasses, Sjogren syndrome dry eye and non-Sjogren syndrome dry eye (primary and secondary lacrimal gland deficiencies, obstruction of the lacrimal gland ducts, reflex hyposecretion, reflex motor block). The latter, EDE, is generally characterized by excessive water loss from the ocular surface due to evaporation. As with ADDE, EDE, can also be divided into two major subclasses—intrinsically caused and extrinsically caused EDE. Intrinsic causes can include inflammation of the meibomian glands which make the lipid or oily part of tears that slows evaporation and keeps the tears stable, eye lid disorders, and infrequent blinking. EDE is often referred to as posterior blepharitis, meibomian gland disease or meibomitis. Extrinsic causes can include other ocular surface disorders, diseases, or infections, contact lens wear, and allergies.

Many ocular surface diseases, including dry eye, are characterized by the presence by a common final pathway of inflammatory related lesions during the examination of the ocular surface. Early signs of ocular surface disease, primary or secondary to inflammation, may further include redness, chemosis, and/or engorged vasculature (usually localized in bulbar or palpebral conjunctiva). Later stage ocular surface disease often manifests further due to inadequate, intermittent, and/or untreated inflammation. Signs and symptoms of mature ocular surface disease include anterior lid margin vascularization around the orifice, obstruction of varying degrees of the meibum secretion, degrees of meibum viscosity and turbidity, zone A posterior lid margin vascularization, chalasis, and meibomian gland loss and/or drop out. These lesions can be accompanied by vascularization suggesting both acute and chronic processes that will be ongoing unless multiple treatment approaches quells the common final pathways promoting the chronic morbidity associated with the varying degrees and frequency of inflammatory insults.

A number of risk factors found to correlate to the development of dry eye have been identified and include being female, older age, postmenopausal estrogen therapy, diabetes, a diet that is low in omega 3 essential fatty acids or has a high ratio of omega 6 to omega 3 fatty acids, refractive surgery, vitamin A deficiency, radiation therapy, bone marrow transplant, hepatitis C, certain classes of systemic and ocular medications including antihistamines (see Smith, 2007). Other risk factors may include autoimmune deficiencies, microbial infection (viral and/or bacterial), connective tissue diseases, systemic cancer chemotherapy, and certain medications (see Smith, 2007).

Current solutions for treating dry eye include tear supplementation (e.g., lubricants), tear retention, tear stimulation, tear substitutes, anti-inflammatory therapy, and essentially fatty acids, and environmental strategies. (see Pflugfelder, *The Ocular Surface* 5(2): 163-178, 2007). Non-limiting examples of current solutions include topical artificial tears, topical cyclosporine A (commercially available as RESTASIS®), systemic omega 3 fatty acids, systemic flaxseed, oral antibiotics (i.e., minocycline, doxycycline, tetracycline, azithromycin), topical antibiotics, oral steroids, topical steroids, topical non-steroidals, topical anti-allergy drops, as well as manual procedures, including mechanical opening and clearing of blocked glands (e.g., LIPIFLOW®), intense pulse light therapy, punctal plugs, and punctal cautery. Of the solutions discussed, lubricants are the easiest, least invasive, and most frequently employed solution to dry eye. The effects of lubricants, however, are ephemeral and require constant reapplication for sustained relief. None of the current solutions are sufficient—a broader spectrum solution is needed to alleviate the symptoms associated with dry eye disease.

The present disclosure relates to the topical treatment of ocular surface diseases, particularly dry eye, with topical applications of at least one aldosterone antagonist in the eye or surrounding adnexal structures surrounding or adjacent to the ocular surface (including the tear film, cornea, conjunctiva including goblet cells, ocular lymphatics, eye lids, eye lid glands including meibomian glands, glands of Zeiss and Wolfring, etc.), as a way of providing therapeutically useful concentrations of the drug at its site of action. This class of topical drugs with its diuretic, antiandrogenic and other unspecified drug actions on the ocular surface may be therapeutic locally while minimizing drug entry into the blood stream, and therefore, preventing or avoiding possible systemic side effects. The topical applications can include other active agents such as antibiotics, including dapsone (diaminodiphenyl sulfone (DDS)).

Aldosterone antagonists have been used in the cosmetic and skin care industries. For example, the aldosterone antagonist spironolactone has been used as an ingredient in cosmetic skin and hair care compositions (U.S. Pat. App. Pub. No. 2010/0029574 and U.S. Pat. No. 7,879,910). Further, spironolactone has been used in the pharmaceutical industries to treat skin conditions (EP Pat. No. 0582458, PCT Pat. App. Pub. No. WO 2010/038234, and U.S. Pat. App. Pub. No. 2013/0143850), and for treating glaucoma (U.S. Pat. No. 3,551,554). The optical correction industry has also employed the use of aldosterone antagonists and methods for producing contact lenses have been described that employ spironolactone among other aldosterone antagonists (US Pat. App. Pub. No.: 2012/0113384). Other methods of using spironolactone are disclosed in U.S. Pat. No. 8,003,690, EP Pat. No. 0126684, U.S. Pat. App. Pub. Nos. 2010/0003354 and 2006/0210604, and PCT Pat. App. Pub. Nos. WO 2012/093117 and WO 2013/170317. Spironolactone is used in the management of hyperaldosteronism, adolescent and adult acne, and female hirsutism. See also, Arita, R., Zavala, M., & Yee, R. W., "MGD Diagnosis," Curr Opthalmol Rep, 49-57 (Jun. 4, 2014); Kim, G. K. and Del Rosso, J. Q., "Oral Spironolactone in Post-teenage Female Patients with Acne Vulgaris," J Clin Aesthet Dermatol, 5(3): 37-50 (March 2012); Tavakkoli, F., "Review of the role of Spironolactone in the therapy of children," 18th Expert Committee on the Selection and Use of Essential Medicines (Mar. 21, 2011).

To date, however, aldosterone antagonists, including spironolactone, have not been used for the treatment of ocular surface disorders, in particular dry eye disease. Aldosterone antagonists are, as the name suggests, receptor antagonists at the mineralocorticoid receptor. Antagonism of these receptors inhibits sodium resorption in the collecting duct of the nephron in the kidneys. This interferes with sodium/potassium exchange, reducing urinary potassium excretion and weakly increasing water excretion (diuresis). Additionally, aldosterone antagonists, such as spironolactone, may also be employed for the purpose of reducing elevated or unwanted androgen activity in the body at its site of action and possibly demonstrating positive clinical effects on the glands of the eye and surrounding structures based on the clinical improvement noted from our patients using a topical eye application.

As provided herein, aldosterone antagonists have been demonstrated to have clinical efficacy in patients who have a variety of symptoms and signs of dry eye ocular surface external disease.

SUMMARY OF THE INVENTION

The present disclosure extends the use of aldosterone antagonists to include use for treating ocular disease, such as ocular surface diseases, and especially dry eye.

Ocular disease that can be treated with methods and/or compositions of the invention can include any ophthalmic condition and or disease, including front of the eye diseases and/or back of the eye diseases, including any related or associated pathways involved in the disease process and treatment. The front of the eye diseases can deal with cellular or subcellular components of the front of the eye anatomy or histology, which includes the acellular tear film layer and its lipid aqueous mucin components. Front of the eye diseases also include diseases to the upper and lower eyelids including disease to the meibomian gland and its cellular and tissue components, (e.g., the muscle, lipid producing holocrine, exocrine and endocrine glands and its vascular and connective tissue components, etc.) as well as the conjunctiva and its associated cells including goblet cells, fibroblast cells, vascular and component blood cells. Front of the eye disorders further encompass any conditions or diseases of the corneal layers including the multi layers of epithelial cells, stromal cells and fibroblasts, corneal endothelial cells, corneal nerve and associated cells and ground substances. Diseases of the front of the eye could include, but is not limited to, inflammation, diffuse lamellar keratitis, corneal diseases, edemas, or opacifications with an exudative or inflammatory component, diseases of the eye that are related to systemic autoimmune diseases, any ocular surface disorders from dry eye (including ADDE, EDE, and chronic dry eye generally, keratoconjunctivitis, such as vernal keratoconjunctivitis, atopic keratoconjunctivitis and sicca keratoconjunctivitis), lid margin diseases, meibomian gland disease or dysfunction, dysfunctional tear syndromes, anterior and/or posterior blepharitis, Staphylococcal blepharitis, microbial infection, computer vision syndrome (e.g., as well as any situations where users are staring at monitors, phones, e-readers, tablets, such as ipads, etc.), conjunctivitis (e.g., persistent allergic, giant papillary, seasonal intermittent allergic, perennial allergic, toxic, conjunctivitis caused by infection by bacteria, fungi, parasites, viruses or *Chlamydia*), conjunctival edema, anterior uveitis, and any inflammatory components or components of the aqueous fluid, inflammatory conditions resulting from surgeries such as LASIK®, LASEK®, refractive surgery, intraocular lens implantation (IOL), irreversible corneal edema as a complication of cataract surgery, edema as a result of insult or trauma (physical, chemical, pharmacological, etc), genetic diseases of the cornea (corneal dystrophies including keratoconus, posterior polymorphous dystrophy; Fuch's dystrophies (corneal and endothelial), etc.), aphakic and pseudophakic bullous keratopathy, scleral diseases with or without inflammatory components, ocular cicatricial pemphigoid, pterygium, etc.

The back of the eye diseases can deal with cellular or subcellular components of the back of the eye anatomy and histology including the retina and all of the 10 or more cells comprising the layers of the retina, e.g., such as photoreceptors outer and inner layers, nuclear cell layers, amacrine and gangion cells, macula, fovea, and vitreous. Additional components of the back of the eye include the ciliary body, iris, uvea and the retinal pigment cells. Back of the eye diseases include processes that involve the optic nerve and its entire cellular and sub cellular components such as the axons and their innervations. These include diseases such as primary open angle glaucoma, acute and chronic closed angle glaucoma and any other secondary glaucomas. Diseases of the back of the eye also may include, but are not limited to, diseases of the optic nerve (including its cellular and sub cellular components such as the axons and their innervations), glaucomas (including primary open angle glaucoma, acute and chronic closed angle glaucoma and any other secondary glaucomas), myopic retinopathies, macular edema (including clinical macular edema or angiographic cystoid macular edema arising from various aetiologies such as diabetes, exudative macular degeneration and macular edema arising from laser treatment of the retina), diabetic retinopathy, age-related macular degeneration, retinopathy of prematurity, retinal ischemia and choroidal neovascularization and like diseases of the retina, genetic disease of the retina and macular degeneration, pars planitis, Posner Schlossman syndrome, Bechet's disease, Vogt-Koyanagi-Harada syndrome, hypersensitivity reactions, toxoplasmosis chorioretinitis, inflammatory pseudotumor of the orbit, chemosis, conjunctival venous congestion, periorbital cellulitis, acute dacryocystitis, non-specific vasculitis; sarcoidosis, cytomegalovirus infection, and the like.

Compositions can comprise an effective amount of at least one aldosterone antagonist, as well as isomers, salts, and solvates thereof, and a carrier, such as a pharmaceutically acceptable carrier. The one or more aldosterone antagonists may be chosen from spironolactone, eplerenone, canrenone (e.g., canrenoate potassium), prorenone (e.g., prorenoate potassium), mexrenone (e.g., mexrenoate potassium), an acceptable isomer, salt or solvate thereof, or combinations comprising the same. Further, the pharmaceutically acceptable carrier may be any carrier. In particular aspects, the carrier may be any one or more of water, an aqueous solution, a polymer such as hydroxypropyl methylcellulose (hypromellose or HPMC), petrolatum, mineral oil, castor oil, carboxymethyl cellulose, polyvinyl alcohol, hydroxypropyl cellulose, hyaluronic acid (hyaluronan or HA), glycerin, polyvinyl alcohol, polyethylene glycol (PEG) such as Polyethylene Glycol 400 (PEG 400), propylene glycol (PG), polysorbate 80, povidone, and/or dextran. The aldosterone antagonist can be present in the carrier by weight or by volume in an amount from 0.05% to 10%, or from 0.05% to 1%, or from 0.05% to 0.5%, or from 0.3% to 0.8% or from 0.4% to 1.2%, or from 0.6% to 1.5%, or from 1% to 2%, or from 3% to 4%, and so on.

Embodiments described herein may provide a composition consisting essentially of at least one aldosterone antagonist (including, isomers, salts, and solvates thereof), and a carrier, such as a pharmaceutically acceptable carrier.

The compositions described herein are useful in various physical forms. Non-limiting examples of acceptable compositional forms include liquids (e.g., eye drops), sprays, suspensions, gels, pastes, ointments, nanosized drug particles, pellets, emulsifications, creams, solids, etc.

It is another object of the embodiments described herein, to provide a method for treating an ocular surface disease, more particularly, dry eye disease. The method comprises topically administering to an ocular region of an animal, such as a mammal (e.g., a human, canine, feline, etc.), a composition comprising an effective amount of at least one aldosterone antagonist (including isomers, salts, and solvates thereof) and a carrier, such as a pharmaceutically acceptable carrier to treat dry eye disease. The compositions can comprise antibiotics and/or steroids or a steroid-like moiety. Compositions comprising an aldosterone antagonist, a steroid, such as prednisone, and/or an antibiotic, such as dapsone are included as embodiments of the invention. Method embodiments may include any of the compositions described herein.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention.

DETAILED DESCRIPTION

Definitions

Figure 1A:
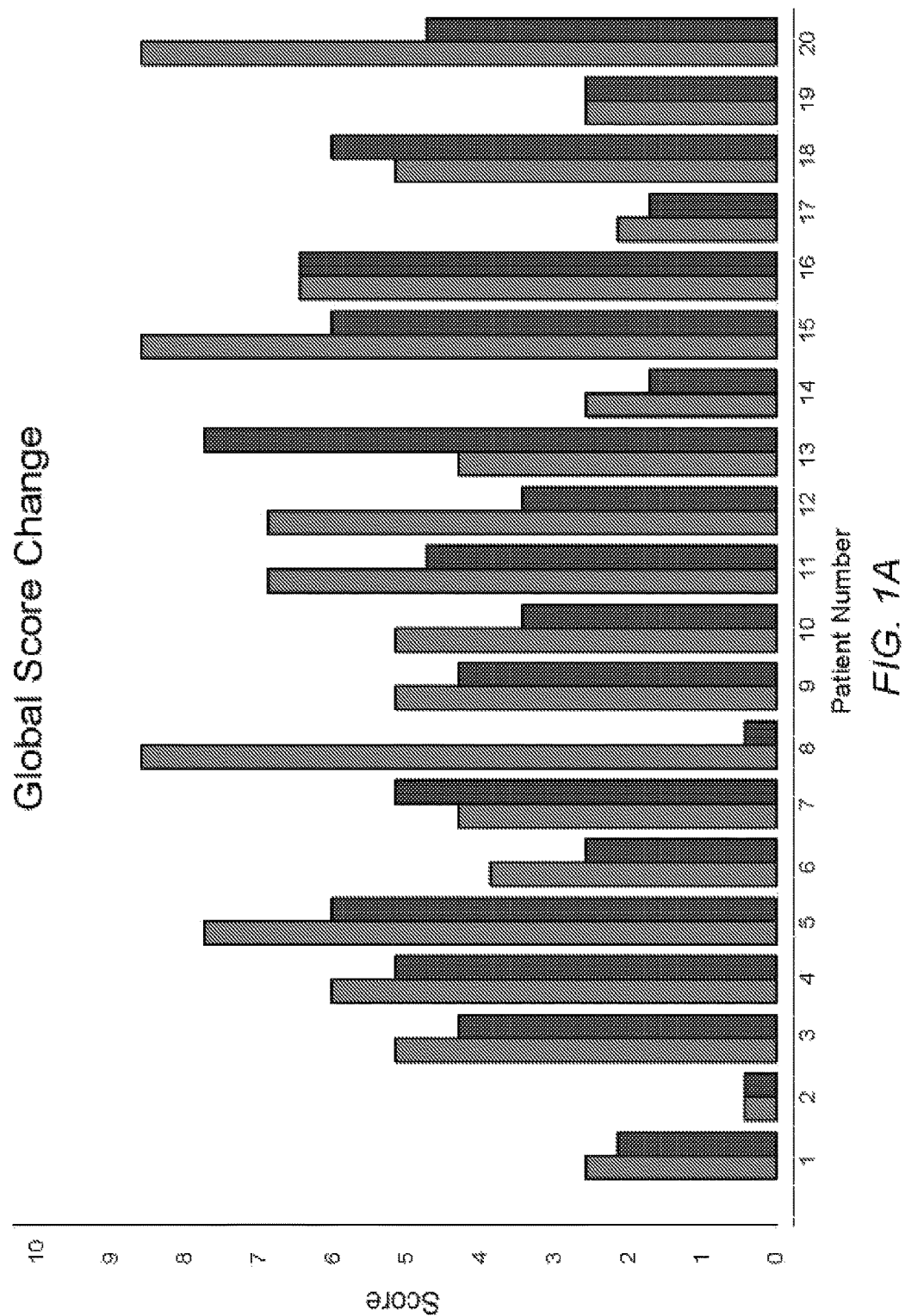
FIG. 1A is a bar graph showing baseline and follow-up Subjective Global Assessment Scores for individual patients of the Pilot Study of Example 3.

As used herein, the singular forms "a", "an" and "the" mean to include the plural forms as well, unless the context clearly indicates otherwise.

As used herein, the terms "administer(s)" "administered", "administering" refers to the placement of a composition into a subject by a method or route which results in at least partial localization of the composition at a desired site such that desired effect is produced. A compound or composition described herein can be administered by any appropriate route known in the art including, but not limited to, topical administration (e.g., ophthalmic drops).

As used herein, the term "aldosterone antagonist(s)" means a compound that suppresses the receptor-mediated activity of aldosterone and/or mineralocorticoid receptors to predict factors which stimulate or suppress aldosterone secretion.

As used herein, the terms "carrier", and "pharmaceutically acceptable carrier" may be used interchangeably, and mean any liquid, suspension, gel, salve, solvent, liquid, diluent, fluid ointment base, nanoparticle, liposome, micelle, giant micelle, and the like, which is suitable for use in contact with a subject without causing adverse physiological responses, and which does not interact with the other components of the composition in a deleterious manner. A number of carrier ingredients are known for use in making topical formulations, such as gelatin, polymers, fats and oils, lecithin, collagens, alcohols, water, etc. The term "pharmaceutically acceptable" means those compounds, materials, compositions, and dosage forms which are, within the scope of sound medical judgment, suitable for use in contact with the tissues of a subject without excessive toxicity, irritation, or other problem or complication, commensurate with a reasonable benefit/risk ratio.

As used herein, the term "isomer(s)" means all stereoisomers of the compounds and/or molecules referred to herein (e.g., aldosterone antagonists, such as spironolactone, eplerenone, canrenone, prorenone, mexrenone, etc., polymers, such as hydroxypropyl methylcellulose, etc.), including enantiomers, diastereomers, as well as all conformers, rotamers, and tautomers, unless otherwise indicated. The compounds and/or molecules disclosed herein include all enantiomers in either substantially pure levorotatory or dextrorotatory form, or in a racemic mixture, or in any ratio of enantiomers. Where embodiments disclose a (D)-enantiomer, that embodiment also includes the (L)-enantiomer; where embodiments disclose a (L)-enantiomer, that embodiment also includes the (D)-enantiomer. Where embodiments disclose a (+)-enantiomer, that embodiment also includes the (−)-enantiomer; where embodiments disclose a (−)-enantiomer, that embodiment also includes the (+)-enantiomer. Where embodiments disclose a (S)-enantiomer, that embodiment also includes the (R)-enantiomer; where embodiments disclose a (R)-enantiomer, that embodiment also includes the (S)-enantiomer. Embodiments are intended to include any diastereomers of the compounds and/or molecules referred to herein in diastereomerically pure form and in the form of mixtures in all ratios. Unless stereochemistry is explicitly indicated in a chemical structure or chemical name, the chemical structure or chemical name is intended to embrace all possible stereoisomers, conformers, rotamers, and tautomers of compounds and/or molecules depicted.

As used herein, the terms "treat", "treating", or "treatment(s)" means the application or administration of a composition described herein, or identified by a method described herein, to a subject, or application or administration of the therapeutic agent to an isolated tissue or cell line from a subject, who has a disease, a symptom of disease, or a predisposition toward a disease, with the purpose to cure, heal, alleviate, relieve, alter, remedy, ameliorate, improve, or affect the disease, the symptoms of disease, or the predisposition toward disease. As used herein, the term "subject" refers to an animal, such as a mammal, including for example a human or domesticated animal (e.g., a dog or cat), which is to be the recipient of a particular treatment.

As used herein, terms "effective amount", "therapeutically effective amount", or "pharmaceutically effective amount" may be used interchangeably and mean the amount of a compound that, when administered to a subject for treating a state, disorder or condition, is sufficient to effect such treatment. The "effective amount" will vary depending on the compound, the disease and its severity, and the age, weight, physical condition and responsiveness of the mammal to be treated.

As used herein, the terms "ocular" or "ocular region" means the eye, surrounding tissues of the eye, and to bodily fluids in the region of the eye. Specifically, the term includes the cornea or, the sclera or, the uvea, the conjunctiva (e.g., bulbar conjunctiva, palpebral conjunctiva, and tarsal conjunctiva), anterior chamber, lacrimal sac, lacrimal canals, lacrimal ducts, medial canthus, nasolacrimal duct, and the eyelids (e.g., upper eyelid and lower eyelid). Additionally, the term includes the inner surface of the eye (conjunctiva overlying the sclera), and the inner surface of the eyelids (e.g., the palpepral conjunctiva).

As used herein, the term "conjunctiva" means the mucous membrane lining the inner surfaces of the eyelids and anterior part of the sclera.

As used herein, the term "cornea" means the clear central frontal tissue of the eye. The degree of corneal curvature varies from subject to subject.

As used herein, the term "eye(s)" means the light sensing organs of a subject and can refer to the sense organ providing vision to a subject.

As used herein, the term "eyelid" means a movable fold of thin skin over the eye, which may further comprise eyelashes and ciliary and meibomian glands along its margin. The eyelid consists of loose connective tissue containing a thin plate of fibrous tissue lined with mucous membrane (conjunctiva).

As used herein, the term "canthus" means either corner of the eye where the upper and lower eyelids meet.

As used herein, the term "mucus" means the viscous, slippery secretions of mucous membranes and glands, containing mucin, white blood cells, water, inorganic salts, and exfoliated cells.

As used herein, the term "lacrimal apparatus" refers to one or more of a lacrimal gland, lacrimal duct, lacrimal sac, or lacrimal canal, or any organ associated with the production or drainage of tears.

As used herein, the term "sclera" means the collagenous outer-wall of the eyeball comprising mostly collagen and some elastic tissue, which is covered by conjunctiva. In humans, the sclera is sometimes referred to as the white of the eye.

As used herein, the term "tear(s)" means the liquid produced by lacrimation, for cleaning and lubricating the eyes.

Compositions

The compositions disclosed comprise an effective amount, such as a pharmaceutically effective amount, of at least one aldosterone antagonist, including isomers, salts, and solvates thereof, as described herein and a carrier, such as a pharmaceutically effective carrier, for administration to an ocular region of a subject to treat an ocular surface disease.

In a particular aspect, the compositions disclosed consist essentially of an effective amount, such as a pharmaceutically effective amount, of at least one aldosterone antagonist, including isomers, salts, and solvates thereof, as described herein and a carrier such as a pharmaceutically effective carrier for administration to an ocular region of a subject to treat an ocular surface disease.

The compositions may be in the form of a liquid (e.g., an ophthalmic drop), a suspension, a gel, a slurry, an ointment, a cream, an emulsion, a solid, a powder of variable sizes macro to nano particle sized (wettable powder or dry powder), or a pellet. In particular aspects, the composition is a liquid composition.

In particular embodiments, the at least one aldosterone antagonists may be chosen from spironolactone, eplerenone, canrenone (e.g., canrenoate potassium), prorenone (e.g., prorenoate potassium), mexrenone (e.g., mexrenoate potassium), an acceptable isomer, salt or solvate thereof, or combinations comprising the same. Further, the pharmaceutically acceptable carrier may be any carrier. In particular aspects, the carrier may be any one or more of water, an aqueous solution, a polymer such as hydroxypropyl methylcellulose (hypromellose or HPMC), petrolatum, mineral oil, carboxymethyl cellulose, polyvinyl alcohol, hydroxypropyl cellulose, hyaluronic acid (hyaluronan or HA), glycerin, polyvinyl alcohol, polyethylene glycol (PEG) such as Polyethylene Glycol 400 (PEG 400), propylene glycol (PG), polysorbate 80, povidone, and/or dextran. The aldosterone antagonist can be present in the carrier by weight or by volume in an amount from 0.05% to 10%, such as from 0.05% to 1%, or from 0.05% to 0.5%, or from 0.3% to 0.8% or from 0.4% to 1.2%, or from 0.6% to 1.5%, or from 1% to 2%, or from 3% to 4%, and so on.

Aldosterone Antagonists:

As disclosed throughout, compositions described herein comprise at least one aldosterone antagonist. The aldosterone antagonists may be a natural aldosterone antagonist, (i.e., not synthetically produced), a synthetic aldosterone antagonist (e.g., a chemically synthesized aldosterone antagonist) or combinations thereof.

In embodiments, aldosterone antagonist(s) may be any aldosterone antagonist or derivative thereof known in the art, including non-limiting representative examples provided in U.S. Pat. No. 4,192,802, U.S. Pat. App. Pub. No. 2003/0199483, U.S. Pat. App. Pub. Nos. 2004/0102423 and 2009/0325918, EP 0046291, and WO 2004/085458, all of which are incorporated by reference herein in their entireties.

Aldosterone antagonists and derivatives can have the following structure:

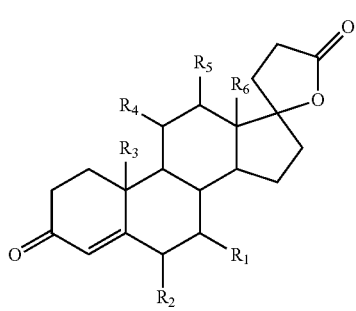

(I)

wherein $R_1$, $R_2$, $R_3$, $R_4$, $R_5$, and $R_6$ may each independently represent a hydrogen atom, an oxygen atom, a halogen atom (e.g., fluorine, chlorine, bromine, iodine), a saturated or unsaturated, branched or unbranched, substituted or unsubstituted aliphatic or aromatic hydrocarbon containing between 1 and 20 carbon atoms, such as an alkyl group, an alkenyl group, an alkynyl group, an alkoxy group, an acyl group, an acetyl group, an aryl group, an aryloxy group, an acrylyl group, a carbonyl group, a cycloalkyl group, a hydroxyalkyl group, an alkoxyalkyl group, a hydroxycarbonyl group, an alkoxycarbonyl group, an acyloxyalkyl group, a heteroaryl group, a heterocyclyl group, a ketal group, an acetal group, an amine group, an amide group, an imide group, an azide group, a sulfur-containing group, a thiol group, a sulfide group, a disulfide group, a sulfinyl group, a sulfonyl group, an acetylthio group, a formyl group, a furyl group, a hydroxyl group, a hetero atom, a cyano group, or an ester, ether, ketone, or aldehyde functional group, as well as substituted groups thereof. When $R_1$ and $R_2$ are each a hydrogen atom, there is a C—C double bond present between the carbon atoms to which $R_1$ and $R_2$ are attached.

For example, in particular embodiments $R_1$, $R_2$, $R_3$, $R_4$, $R_5$, and $R_6$ may each independently represent a methyl group, an ethyl group, a propyl group, a butyl group, a cyclopropyl group, a cyclobutyl group, a cyclopentyl group, a cyclohexyl group, a cycloheptyl group, a methoxy group, an ethoxy group, a propoxy group, a butoxy group, an acetyl group, a propionyl group, a butyryl group, a hydroxymethyl group, a hydroxyethyl group, a hydroxypropyl group, a hydroxybutyl group, a methoxymethyl group, a methoxyethyl group, a methoxypropyl group, a methoxybutyl group, an ethoxy group, an ethoxymethyl group, an ethoxyethyl group, an ethoxypropyl group, an ethoxybutyl group, a propoxymethyl group, a propoxyethyl group, a propoxypropyl group, a propoxybutyl group, a butoxymethyl group, a butoxyethyl group, a butoxypropyl group, a butoxybutyl group, a methoxycarbonyl group, an ethoxycarbonyl group, a propoxycarbonyl group, a butoxycarbonyl group, an acetoxymethyl group, an acetoxyethyl group, an acetoxypropyl group, an acetoxybutyl group, a propionyloxymethyl group, a propionyloxyethyl group, a butyryloxymethyl group, a butyryloxyethyl group, a phenoxy group, a phenyl group, a benzyl group, a benzoyl group, a benzoxy group, a pyrrolyl group, an imidazolyl group, a thiazolyl group, a pyridyl group, a pyrimidyl group, an oxazolyl group, an acetylthio group, a furyl group, a thienyl group, an epoxy group, or substituted groups thereof.

In one embodiment, the at least one aldosterone antagonist is one or more aldosterone antagonist selected from the group consisting of spironolactone, eplerenone, canrenone, prorenone, mexrenone, and combinations thereof, as well as isomers, salts, and solvates thereof In a particular aspect, the at least one aldosterone antagonist is spironolactone, including derivatives, isomers, salts, and solvates thereof. Spironolactone is an aldosterone antagonist of Structure (I) above where $R_1$ is an acetylthio group, $R_3$ and $R_6$ are each a methyl group, and $R_2$, $R_4$, and $R_5$ are each a hydrogen atom. Spironolactone derivatives comprising Structure II (below) and any one or more of the substituents mentioned above for Structure I are also included. Spironolactone refers to aldactone, 3-(3-oxo-7α-acetylthio-17β-hydroxy-androst-4-en-17α-ylu) propiolactone. Spironolactone, commercially available as ALDACTONE® from Pfizer and also referred to as 7α-acetylthio-3-oxo-17α-pregn-4-ene-21,17-carbolactone or 17-hydroxy-7α-mercapto-3-oxo-17α-pregn-4-ene-21-carboxylic acid, γ-lactone acetate, has the molecular formula $C_{24}H_{32}O_4S$ and a molar mass of 416.574 g mol$^{-1}$. Spironolactone has the following structure (II):

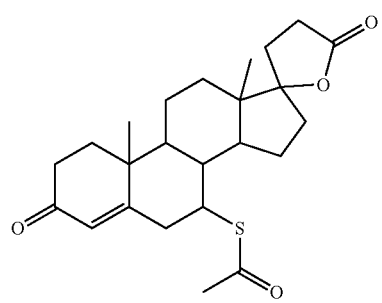

(II)

In particular embodiments, $R_1$ of Structure I above can be an ester functional group namely —COOR', $R_2$ is a hydrogen atom, $R_3$ is a methyl group, $R_4$ is an oxygen atom and forms a 3-membered heterocyclic ring together with the carbon atom to which it is attached and an adjacent carbon atom, $R_5$ is a hydrogen atom, and $R_6$ is a methyl group. In a particular aspect, R' of the —COOR' group can be a $C_{1-10}$ alkyl group, such as a methyl ethyl, propyl, or butyl group.

In another particular aspect, the at least one aldosterone antagonist is eplerenone, including derivatives, isomers, salts, and solvates thereof. Eplerenone is an aldosterone antagonist of Structure (I) above where $R_1$ is a —COOR' group, $R_2$ and $R_5$ are each a hydrogen atom, R', $R_3$, and $R_6$ are each a methyl group, and $R_4$ is an oxygen atom that forms a 3-membered heterocyclic ring together with the carbon atom of the ring to which it is attached and an adjacent carbon atom in the ring. Eplerenone derivatives comprising Structure III (below) and any one or more of the substituents mentioned above for Structure I are also included. Eplerenone is commercially available as INSPRA® from Pfizer, also referred to as pregn-4-ene-7,21-dicarboxylic acid, 9,11-epoxy-17-hydroxy-3-oxo, γ-lactone, methyl ester (7α,11α,17α), has the molecular formula $C_{24}H_{30}O_6$, a molar mass of 414.49 g mol$^{-1}$, and the following structure (III):

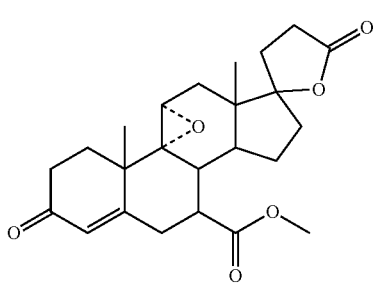

(III)

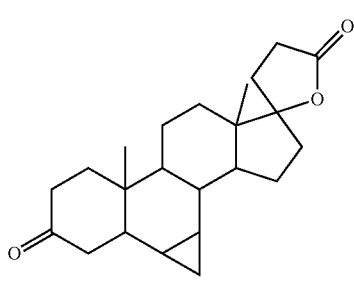

(V)

In another particular aspect, the at least one aldosterone antagonist is canrenone, including derivatives, isomers, salts, and solvates thereof. Canrenone is an aldosterone antagonist of Structure (I) above where $R_3$ and $R_6$ are each a methyl group, $R_1$ and $R_2$ are each a hydrogen atom, and there is a double bond present between the carbon atom on which is attached $R_1$ and the carbon atom on which is attached $R_2$. Canrenone derivatives comprising Structure IV (below) and any one or more of the substituents mentioned above for Structure I are also included. Canrenone may otherwise be referred to as 10,13-dimethylspiro[2,8,9,11,12,14,15,16-octahydro-1H-cyclopenta[a]phenanthrene-17,5'-oxolane]-2',3-dione, has the molecular formula $C_{22}H_{28}O_3$, a molar mass of about 340.456 g mol$^{-1}$, and has the following structure (IV):

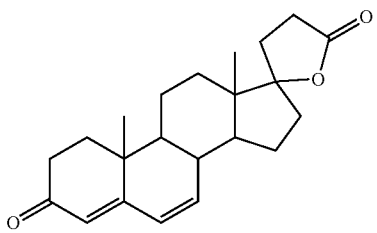

(IV)

In another particular aspect, the at least one aldosterone antagonist is prorenone, including derivatives, isomers, salts, and solvates thereof. Prorenone is an aldosterone antagonist of Structure (I) above with no C—C double bonds and where $R_1$ is a $C_1$ alkyl group ($CH_2$) and forms a 3-membered ring together with the carbon atom of the ring to which it is attached and an adjacent carbon atom in the ring, $R_3$ and $R_6$ are each a methyl group, $R_2$, $R_4$ and $R_5$ are each a hydrogen atom. Prorenone derivatives comprising Structure V (below) and any one or more of the substituents mentioned above for Structure I are also included. Prorenone, also referred to as 3-(17β-hydroxy-6β,7β-methylene-3-oxo-4-androsten-17α-yl)propionic acid γ-lactone, has the molecular formula $C_{23}H_{30}O_3$, a molar mass of about 354.48 g mol$^{-1}$, and the following structure (V):

In another particular aspect, the at least one aldosterone antagonist is mexrenone, including derivatives, isomers, salts, and solvates thereof. Mexrenone is an aldosterone antagonist of Structure (I) above where $R_1$ is a —COOR' group, $R_2$, $R_4$, and $R_5$ are each a hydrogen atom, R', $R_3$, and $R_6$ are each a methyl group. Mexrenone derivatives comprising Structure VI (below) and any one or more of the substituents mentioned above for Structure I are also included. Mexrenone, also referred to as 17-hydroxy-3-oxo-17α-pregn-4-ene-7α,21-dicarboxylic acid 7-methyl ester gamma-lactone, has the molecular formula $C_{24}H_{32}O_5$ and a molar mass of about 400.51 g mol$^{-1}$. Mexrenone has the following structure (VI):

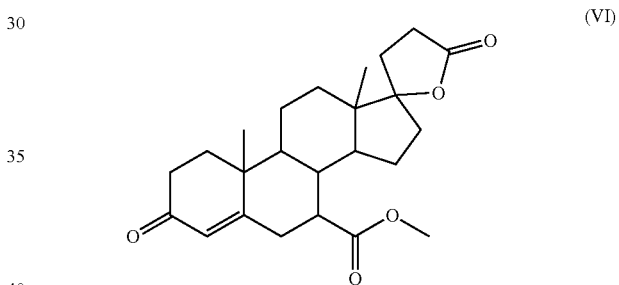

(VI)

In a particular aspect, the at least one aldosterone antagonists used in the compositions described herein may be at least two of the above aldosterone antagonists (i.e., at least two of spironolactone, eplerenone, canrenone, prorenone, mexrenone), at least three of the above aldosterone antagonists, at least four of the above aldosterone antagonists, up to and including all of the above aldosterone antagonists, including isomers, salts, and solvates thereof.

Pharmaceutically Acceptable Carriers:

The carriers (e.g., pharmaceutically acceptable carriers) described herein will allow the one or more aldosterone antagonist(s) to remain efficacious (e.g., capable of treating an ocular surface disease, such as, dry eye). Non-limiting examples of carriers described herein include liquids, suspensions, gels, ointments, nanosized drug particles, pellets, slurries, or solids (including wettable powders or dry powders). The selection of the carrier material will depend on the intended application.

Carriers and pharmaceutically acceptable carriers for use with the compositions of the present invention are well known in the pharmaceutical arts. Non-limiting examples of such carriers include such vehicles as water; organic solvents, alcohols, lower alcohols that are readily capable of evaporating from the skin, ethanol, glycols, glycerin, aliphatic alcohols, mixtures of water and organic solvents, mixtures of water and alcohol, mixtures of organic solvents such as alcohol and glycerin, lipid-based materials such as fatty acids, acylglycerols, oils, mineral oils, fats of natural or synthetic origin, phosphoglycerides, sphingolipids, waxes, DMSO, protein-based materials such as collagen and gelatin, volatile and/or non-volatile silicon-based materials, cyclomethicone, dimethiconol, dimethicone copolyol (Dow Corning, Midland, Mich., USA), hydrocarbon-based materials such as petrolatum and squalane, sustained-release vehicles such as microsponges and polymer matrices, suspending agents, emulsifying agents, and other vehicles and vehicle components that are suitable for administration to the ocular region, as well as mixtures of topical vehicle components as identified above or otherwise known to the art.

The carrier may also be a commercially available neutral base known in the art. A neutral base has no significant therapeutic effect of its own. It simply conveys the active pharmaceutical ingredient, although some vehicles may do so with greater ease or effectiveness than others. A neutral base may be a cream used cosmetically for softening and/or cleaning the skin. Non-limiting examples include EUCERIN® (Beiersdorf Aktiengesellschaft Corp., Hamburg, Germany), AQUAPHOR® (Beiersdorf Aktiengesellschaft Corp., Hamburg, Germany), and liposomal vehicles. A preferred neutral base is VANICREAM® (Pharmaceutical Specialties, Inc., Rochester, Minn., USA). VANICREAM® is composed of purified water, white petrolatum, cetearyl alcohol and ceteareth-20, sorbitol solution, propylene glycol, simethicone, glyceryl monostearate, polyethylene glycol monostearate, sorbic acid, and butylated hydroxytoluene (BHT).

The compositions or carriers may be a transdermal gel such as Pluronic Lecithin Organogel (PLO). See Murdan, A Review of Pluronic Lecithin Organogel as a Topical and Transdermal Drug Delivery System, Hospital Pharmacist, July/August 2005, Vol. 12, pp. 267-270.

In particular embodiments, the carrier is a polymer. Non-limiting examples of acceptable polymers include, hydroxyethyl cellulose, hydroxypropyl methyl cellulose, carboxymethyl cellulose (e.g., cellulose, or Gum Cellulose), polyethylene oxide, dextrans, and the like.

In a more particular embodiment, the carrier is hydroxypropyl methyl cellulose (HPMC) (also referred to as hypromellose).

Additional Compounds:

The compositions and/or carriers provided herein may include one or more additional compounds, or be used contemporaneously (e.g., used separately but with the compositions and/or carriers described herein) with, one or more additional compounds. Additional compounds may include antibiotics, steroids, anti-inflammation agents, analgesics, surfactants, chelating agents, buffering agents, pH adjusting agents, adjuvants, or combinations thereof. The additional compounds can provide any purpose, so long as the additional compounds are suitable for use in a composition or carrier used on a subject. Beneficial purposes of additional compounds may include synergistic effects when combined with the active ingredients of the composition (i.e., a greater than additive effect), composition and/or carrier stabilization, enhanced delivery of the compositions to the subject, ease of formulating, and combinations thereof.

Antibiotics:

In some aspects, the compositions and/or carriers may further include at least one antibiotic. The antibiotic may be any antibiotic suitable for use in a subject, in particular a mammalian subject, and more particularly, in a human subject. Non-limiting examples of antibiotics that may be used with the compositions and/or carriers described herein include amikacin, gentamicin, kanamycin, neomycin, netilmicin, streptomycin, tobramycin, teicoplanin, vancomycin, azithromycin, clarithromycin, dirithromycin, erythromycin, roxithromycin, troleandomycin, amoxicillin, ampicillin, azlocillin, carbenicillin, clozacillin, dicloxacillin, flucozacillin, meziocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflazacin, trovafloxacin, mafenide, sulfacetamide, sulfamethizole, sulfasalazine, sulfisoxazole, trimethoprim, cotrimoxazole, demeclocycline, soxycycline, minocycline, oxytetracycline, tetracycline, vancomycin, and salts thereof, and the like. Additionally, the antibiotics may include any sulfone such as dapsone (diaminodiphenyl sulfone (DDS)) or any dapsone derivative, such as amino acid amides of dapsone (see Pochopin et al., International Journal of Pharmaceutics, 121(2):157-167 (1995)), PROMIN (sodium glucosulfone), DIASONE (sulfoxone sodium), SULPHETRONE (solapsone), PROMIZOLE (thiazolsulfone), PROMACETIN (acetosulfone) and the like. Additional sulfones have been described (see Doub, Medicinal Chem, 5:350-425 (1961)). In any embodiment of the methods described in this disclosure, a sulfone such as dapsone may be administered to an ocular region of a subject with at least one aldosterone antagonist, or isomer, salt, or solvate thereof. The sulfone and at least one aldosterone antagonist may be administered in the same composition or in separate compositions, and may be administered simultaneously or sequentially one to the other. In embodiments, dapsone can be present in the composition in an amount ranging from 0.0005 wt % to 10 wt %, such as from 0.05 wt % to 5 wt %, or from 0.1 wt % to 3 wt %, or from 0.5 wt % to 0.8 wt %, or from 0.7 wt % to 4 wt % based on the total weight of the composition. Dapsone can be present in the composition with an amount of aldosterone antagonist (such as spironolactone) ranging from about 0.0005 wt % to 10 wt %, such as from about 0.0005 wt % to 1 wt %, or from 0.005 wt % to 5 wt %, or from 0.05 wt % to 3 wt %, or from about 0.5 wt % to 2 wt %, or from 0.07 wt % to about 6 wt % based on the total weight of the composition.

Steroidal Compounds:

In another aspect, the compositions and/or carriers may further include at least one steroid. The steroid may be any steroid suitable for use in a subject, in particular a mammalian subject, and more particularly, in a human subject. Non-limiting examples of steroids that may be used with the compositions and/or carriers described herein include 21-acetoxypregnenolone, acetonide, alclomethasone, algestone, amcinonide, beclomethasone, betamethasone, budesonide, chenodeoxycholic acid, chloroprednisone, clobetasol, clobetasone, clocortolone, cloprednol, corticosterone, cortisone, cortivazol, deflazacort, desonide, desoximethasone, dexamethasone, diflorasone diflucortolone, difluprednate, ethynylestradiol, estradiol, fluazacort, flucloronide, flumethasone, flunisolide, fluocinolone acetonide, fluocinonide, fluocortyn butyl, fluocortolone, fluorometholone, fluticasone propionate, fluperolone acetate, fluprednidene acetate, fluprednisolone, flurandrenolide, formocortal, halcinonide, halobetasol propionate, halomethasone, halopredone acetate, hexacetonide, hydrocortamate, hydrocortisone, loteprednol etabonate, mazipredone, medrysone, meprednisone, mestranol, methylprednisolone, mitatrienediol, momethasone furoate, moxestrol, paramethasone, prednicarbate, prednisolone, prednisolone 25-diethylaminoacetate, prednisolone sodium phosphate, prednisone, prednival, prednylidene, rimexolone, triamcinolone, triamcinolone, tixocortol, triamcinolone, ursodesoxycholic acid, and salts thereof, and the like.

Anti-Inflammatory Agents:

In yet other aspects, the compositions and/or carriers may further include at least one anti-inflammatory agent. The anti-inflammatory agent may be any anti-inflammatory agent suitable for use in a subject, in particular a mammalian subject, and more particularly, in a human subject. Non-limiting examples of anti-inflammatory agents include aceclofenac, acemetacin, acetylsalicylic acid, 5-amino-acetylsalicylic acid, alclofenac, alminoprofen, amfenac, bendazac, bermoprofen, α-bisabolol, bromfenac, bromosaligenin, bucloxic acid, butibufen, carprofen, cinmetacin, clidanac, clopirac, diclofenac sodium, diflunisal, ditazol, enfenamic acid, etodolac, etofenamate, felbinac, fenbufen, fenclozic acid, fendosal, fenoprofen, fentiazac, fepradinol, flufenamic acid, flunixin, flunoxaprofen, flurbiprofen, glucametacin, glycol salicylate, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, naproxen, niflumic acid, oxaceprol, oxaprozin, oxyphenbutazone, parsalmide, perisoxal, phenyl acetylsalicylate, olsalazine, pyrazolac, piroxicam, pirprofen, pranoprofen, protizinic acid, salacetamide, salicilamide O-acetic acid, salicylsulphuric acid, salsalate, sulindac, suprofen, suxibuzone, tenoxicam, tiaprofenic acid, tiaramide, tinoridine, tolfenamic acid, tolmetin, tropesin, xenbucin, ximoprofen, zaltoprofen, zomepirac, tomoxiprol or sulindac, salts thereof, and the like.

Analgesics:

In yet other aspects, the compositions and/or carriers may further include at least one analgesic. The analgesic may be any analgesic suitable for use in a subject, in particular a mammalian subject, and more particularly, in a human subject. Non-limiting examples of analgesics include acetaminophen (i.e., paracetamol), acetaminosalol, aminochlorthenoxazin, acetylsalicylic 2-amino-4-picoline acid, acetylsalicylsalicylic acid, anileridine, benoxaprofen, benzylmorphine, 5-bromosalicylic acetate acid, bucetin, buprenorphine, butorphanol, capsaicine, cinchophen, ciramadol, clometacin, clonixin, codeine, desomorphine, dezocine, dihydrocodeine, dihydromorphine, dimepheptanol, dipyrocetyl, eptazocine, ethoxazene, ethylmorphine, eugenol, floctafenine, fosfosal, glafenine, hydrocodone, hydromorphone, hydroxypethidine, ibufenac, p-lactophenetide, levorphanol, meptazinol, metazocine, metopon, morphine, nalbuphine, nicomorphine, norlevorphanol, normorphine, oxycodone, oxymorphone, pentazocine, phenazocine, phenocoll, phenoperidine, phenylbutazone, phenylsalicylate, phenylramidol, salicin, salicylamide, tiorphan, tramadol, diacerein, actarit or salts thereof, and the like.

Surfactants/Wetting Agents:

In some aspects, the compositions and/or carriers may also include at least one surfactant or wetting agent. The surfactant may be selected from, but is not limited to, anionic, cationic, amphoteric, zwitterionic, and nonionic surfactants. If the surfactant is nonionic, it may be selected from the group consisting of polysorbates, poloxamers, alcohol ethoxylates, ethylene glycol-propylene glycol block copolymers, fatty acid amides, alkylphenol ethoxylates, or phospholipids, and the like.

Chelating Agents:

In still other aspects, the compositions and/or carriers may also include a chelating agent, including but not limited to, edetate salts, like edetate disodium, edetate calcium disodium, edetate sodium, edetate trisodium, edetate dipotassium, and the like.

Buffering Agents:

In yet other aspects, the compositions and/or carriers may also include at least one buffer. Non-limiting examples of buffers may include phosphates (e.g., sodium phosphate, sodium dihydrogen phosphate, disodium hydrogen phosphate, potassium phosphate, potassium dihydrogen phosphate and dipotassium hydrogen phosphate, etc.), borates (e.g., sodium borate, potassium borate, etc.) citrates (e.g., sodium citrate, disodium citrate, etc.), acetates (e.g., sodium acetate, potassium acetate, etc.) carbonates (e.g., sodium carbonate, sodium hydrogen carbonate, etc.), and the like.

pH Adjusting Agents:

In yet still other aspects, the compositions and/or carriers may also include at least one pH adjusting agent. Non-limiting examples of pH adjusting agents include sodium hydroxide, potassium hydroxide, sodium carbonate, hydrochloric acid, phosphoric acid, citric acid, acetic acid, and the like.

Preservatives:

In still yet other aspects, the compositions and/or carriers may be preservative free or may also include at least one preservative. Non-limiting examples of preservatives include p-hydroxy benzoate esters, benzalkonium chloride, benzethonium chloride, chlorobutanol, benzyl alcohol, sorbic acid or its salts, chlorhexidine gluconate, sodium dehydroacetate, cetylpyridinium chloride, alkyldiaminoethylglycine hydrochloride. Other compounds that may be included in the compositions and/or carriers can include oleic acid, 1-methyl-2 pyrrolidone, 2,2-dimethyl octanoic acid and N,N dimethyl lauramide/propylene glycol monolaureate or combinations thereof, which may be included for example to minimize the barrier characteristics of the upper most layer of the corneal and conjunctival surfaces, thus, improving efficacy.

Adjuvants:

Further still, the compositions or carriers provided herein, may also include one or more adjuvants. Non-limiting examples of suitable adjuvants include phosphatidic acid, sterols such as cholesterol, aliphatic amines such as stearylamine, saturated or unsaturated fatty acids such as stearic acid, palmitic acid, myristic acid, linoleic acid, oleic acid, and salts thereof, and the like.

Methods

Further disclosed are methods for treating at least one ocular surface disease comprising administering to an ocular region of a subject one or more of the compositions described herein.

In another aspect, methods for treating at least one ocular surface disease comprise administering a composition comprising a pharmaceutically effective amount of at least one aldosterone antagonist (including isomers, salts, and solvates thereof) and a carrier to the ocular region of a subject.

In still a more particular aspect of the disclosed methods, the composition described herein is a composition that delivers at least one aldosterone antagonist (including isomers, salts, and solvates thereof) having a desired therapeutically effective amount of aldosterone antagonist in the range of about 0.0005 wt. % to 1.00 wt. % of the composition or carrier to the ocular region of a subject to be treated. It is envisioned that the therapeutically effective amount of the at least one aldosterone antagonist could be greater than 1.00 wt. % depending what can be tolerated by the subject being treated and the clinical effect(s) at the site of action (ocular surface anatomical structures, including the cornea, conjunctiva, lid margin epithelium, blood vessels, the meibomian gland/sebaceous gland complex, etc.). As provided throughout, the aldosterone antagonists used to carry out the methods described herein can be any aldosterone antagonist or isomer, salt, or solvate thereof. In particular aspects, the aldosterone antagonist is spironolactone or an isomer, salt or solvate thereof.

In a particular aspect, the methods described herein treat front of the eye ocular surface diseases. In another aspect, the methods described herein treat back of the eye ocular surface diseases. In still another aspect, the methods described herein treat both front of the eye diseases and back of the eye diseases.

Non-limiting examples of front of the eye ocular surface diseases include inflammation, diffuse lamellar keratitis, corneal diseases, edemas, or opacifications with an exudative or inflammatory component, diseases of the eye that are related to systemic autoimmune diseases, any ocular surface disorders from dry eye (including ADDE, EDE, and chronic dry eye generally, keratoconjunctivitis, such as vernal keratoconjunctivitis, atopic keratoconjunctivitis, and sicca keratoconjunctivitis), lid margin diseases, meibomian gland disease or dysfunction, dysfunctional tear syndromes, anterior and or posterior blepharitis, microbial infection, computer vision syndrome, conjunctivitis (e.g., persistent allergic, giant papillary, seasonal intermittent allergic, perennial allergic, toxic, conjunctivitis caused by infection by bacteria, fungi, parasites, viruses or *Chlamydia*), conjunctival edema anterior uveitis and any inflammatory components or components of the aqueous fluid, inflammatory conditions resulting from surgeries such as LASIK®, LASEK®, refractive surgery, intraocular lens implantation (IOL), irreversible corneal edema as a complication of cataract surgery, edema as a result of insult or trauma (physical, chemical, pharmacological, etc), genetic diseases of the cornea (corneal dystrophies including keratoconus, posterior polymorphous dystrophy; Fuch's dystrophies (corneal and endothelial), etc.), aphakic and pseudophakic bullous keratopathy, scleral diseases with or without inflammatory components, ocular cicatrcial pemphigoid, pterygium, and the like.

Non-limiting examples of back of the eye diseases include diseases of the optic nerve (including its cellular and sub cellular components such as the axons and their innervations), glaucomas (including primary open angle glaucoma, acute and chronic closed angle glaucoma and any other secondary glaucomas), myopic retinopathies, macular edema (including clinical macular edema or angiographic cystoid macular edema arising from various etiologies such as diabetes, exudative macular degeneration and macular edema arising from laser treatment of the retina), diabetic retinopathy, age-related macular degeneration, retinopathy of prematurity, retinal ischemia and choroidal neovascularization and like diseases of the retina, genetic disease of the retina and macular degeneration, pars planitis, Posner Schlossman syndrome, Bechet's disease, Vogt-Koyanagi-Harada syndrome, hypersensitivity reactions, toxoplasmosis chorioretinitis, inflammatory pseudotumor of the orbit, chemosis, conjunctival venous congestion, periorbital cellulitis, acute dacryocystitis, non-specific vasculitis, sarcoidosis, cytomegalovirus infection, and the like.

In particular aspects, the methods described herein treat dry eye (including ADDE, EDE, chronic dry eye, etc.).

In embodiments, compositions described herein are administered to the ocular region of a subject by topical administration. In one aspect, there is provided a method for treating dry eye, the method comprising: topically administering to an ocular region of a subject a composition comprising spironolactone and hydroxypropyl methylcellulose, and/or optionally comprising one or more preservatives, and/or optionally comprising one or more compounds for increasing efficacy; and reducing or preventing one or more symptoms or causes of dry eye. In embodiments the spironolactone of the compositions can be substituted with or supplemented with one or more of eplerenone, canrenone, prorenone, and/or mexrenone.

In still other embodiments, the compositions are administered with one or more additional pharmaceutical agents. The one or more additional pharmaceutical agents may be administered, before, after, or simultaneously with the administration of the compositions described herein. In one aspect, the one or more additional pharmaceutical agents is administered before the administration of the compositions described herein. In another aspect, the one or more additional pharmaceutical agents is administered after the compositions described herein. In still yet another aspect, the one or more additional pharmaceutical agents is administered simultaneously with the administration of the compositions described herein. In embodiments where the one or more additional pharmaceutical agents is administered simultaneously with the administration of the compositions, the additional pharmaceutical agent may be formulated with the compositions described herein or administered as a separate pharmaceutical agent at about the same time as the compositions described herein are administered.

Such methods can comprise administering a composition comprising from between 0.05% and 10%, such as from between 0.05% and 1%, or from between 0.1% and 1%, or from between 0.15% and 0.8%, or from between 0.2% and 0.7%, or from between 0.3% and 0.5%, or from between 0.4% and 0.9% spironolactone, eplerenone, canrenone, prorenone, and/or mexrenone (based on weight or volume of the composition). Such methods can include administering the composition from between 1-8 times daily; and/or from between 1-4 times daily, for 1-4 weeks; and/or from between 1-4 times daily, for up to 4 weeks, then from 1-2 times daily. For some patients, it may be expected that the compositions can be administered indefinitely, permanently, or otherwise on a long-term basis as a maintenance therapy. In some, instances, the method can include administering the compositions described herein to a subject throughout the lifetime of the subject as a maintenance therapy.

The method can be used to prevent and/or reduce one or more symptoms and/or causes of dry eye such as impaired vision, burning sensation, redness, irritation, grittiness, filminess, inflammation, discomfort, pain, chemosis, chalasis, engorged vasculature, anterior lid margin vascularization, zone A posterior lid margin vascularization, or meibomian gland obstruction, secretion, viscosity, turbidity, loss, drop out, or dysfunction. According to methods of the invention, the reducing or preventing of symptoms or causes of dry eye is quantitatively or qualitatively evidenced by vital staining, such as by lissamine green staining.

In an aspect, the compositions described herein are topically administered to the eye to treat dry eye. In a particular aspect, the compositions described herein are topically administered to the cornea to treat dry eye. In still another particular aspect, the compositions described herein are topically administered to the sclera to treat dry eye. In still yet another particular aspect, the compositions described herein are topically administered to the conjunctiva to treat dry eye. In yet still another particular aspect, the compositions described herein are topically administered to the lacrimal sac to treat dry eye. In another particular aspect, the compositions described herein are topically administered to the lacrimal canals to treat dry eye. In still another particular aspect, the compositions described herein are topically administered to the lacrimal ducts to treat dry eye. In yet another particular aspect, the compositions described herein are topically administered to the canthus to treat dry eye. In still yet another particular aspect, the compositions described herein are topically administered to the eyelids to treat dry eye.

In one aspect, the compositions described herein are topically administered by administering a liquid (e.g., ophthalmic drops) to the ocular region of a subject for example to treat dry eye. In yet another particular aspect, the compositions described herein are topically administered by administering a suspension to the ocular region of a subject for example to treat dry eye. In another particular aspect, the compositions described herein are topically administered by administering a cream to the ocular region of a subject for example to treat dry eye. In still another particular aspect, the compositions described herein are topically administered by administering an emulsion to the ocular region of a subject for example to treat dry eye. In yet another particular aspect, the compositions described herein are topically administered by administering a gel to the ocular region of a subject for example to treat dry eye. In still yet another particular aspect, the compositions described herein are topically administered by administering a paste, pellet, ointment, spray, or nanoparticle vehicle to the ocular region of a subject for example to treat dry eye. In preferred embodiments, the composition comprises xanthan gum. In yet still another particular aspect, the compositions described herein are topically administered by administering a gel to the ocular region of a subject for example to treat dry eye. In another particular aspect, the compositions described herein are topically administered by administering an ointment to the ocular region of a subject for example to treat dry eye. In still another particular aspect, the compositions described herein are topically administered by administering a particle (e.g., a nanosized or macrosized particle, pellet, etc.) to the ocular region of a subject for example to treat dry eye. In yet another particular aspect, the compositions described herein are topically administered by administering a slurry to the ocular region of a subject for example to treat dry eye.

The administering step can be performed by any method known in the art (e.g., liquid dropper, nanoparticle vehicles, gum materials (e.g., xanthan gum materials, sprays, application of the compositions described herein to a material worn over the eye, such as a patch, contact lenses, etc.). Further, the step of administering the compositions provided herein may be repeated as necessary (e.g., more than once, as in the administering step is repeated twice, three times, four times, five times, six times, seven times, eight times, nine times, ten times, eleven times, twelve times, thirteen times, fourteen times, fifteen times, sixteen times, seventeen times, eighteen times, nineteen times, twenty times, etc.) until the ocular surface disease is treated.

The aldosterone antagonist, alone or in combination with other active agents, such as dapsone and/or prednisone, or a preparation comprising these components, can be injected subconjunctivally as well as subtarsally into the eye lids and/or Meibomian glands directly.

EXAMPLES

The following examples are provided for illustrative purposes and are not intended to limit the scope of the embodiments as claimed herein. Any variations in the exemplified examples which occur to the skilled artisan are intended to fall within the scope of the present disclosure.

Example 1: Preparation of the Composition

Materials:
Aldosterone Antagonist:
Spironolactone powder (0.001 to 0.01 g) (Letco Medical, Decatur, Ala., USA) or (PCCA, Houston, Tex., USA) (or an equivalent amount of eplerenone, canrenone, prorenone, and/or mexrenone, or combinations with spironolactone).
Carrier
Hypromellose—PF (preservative free 0.3% solution of Hypromellose without sodium chloride; buffered with sodium phosphate) (Prepared by Greenpark Pharmacy of Houston, Tex.).
Methods:
In a glass mortar with pestle, wet the spironolactone with drops of hypromellose (HPMC) until a paste is made. Preferably, the HPMC starting material for mixing with the aldosterone agent comprises from 0.01% to 5% HPMC, such as from 0.05% to 0.8%, or from 0.1% to 0.5%, or from 0.2% to 1%, or from 0.3% to 2%, or from 0.4% to 3%, or from 0.5% to 4%, and is preservative free. Continue to gradually add the hypromellose until a total amount of approximately 90% to 99.9% by weight of the total composition is the HPMC starting material and is mixed to make a suspension of the spironolactone. Preferably, in the finished product, approximately 91% to 99.8% HPMC starting material is used (percent by weight of the total composition), such as from about 92% to 99.7%, or from about 93% to 99.6%, or from about 94% to 99.5%, or from about 95% to 99.4%, or from about 96% to 99.3%, or from about 97% to 99.2%, or from about 98% to 99.1%, or about 99%. Transfer the suspension into proper size amber glass vial with a spin bar. Cap and seal the vial. Ensure proper size vial is selected to leave enough head space in top of the vial to prevent the cap from coming off during autoclaving. Autoclave the vial with the contents. Immediately after autoclave, place vial onto a hot plate spin bar stirrer. Spin bar stir the suspension over night at room temperature. Transfer 15 ml into each drop container. Sterilization procedures can be used in addition to or alternatively to autoclaving. Any known sterilization procedure or combinations of such procedures can be used. Discard any remaining contents 30 days after opening. (preservative free).

Example 2: Administering the Composition to a Subject

A composition of Example 1 is administered to a number of subjects. The subjects are instructed to administer the composition of Example 1 to the eye up to four-times a day using ophthalmic drops for 1-4 weeks.

Results indicate that after two weeks of treatment using the composition of Example 1 as instructed, the subjects are reporting less redness, less irritation, less grittiness, and greater tolerance for their symptoms.

Quantitative results indicate that patients using the composition of Example 1 as instructed tend to have less conjunctival redness, improved obstruction of the meibomian glands, and/or improved turbidity of the glands. Quantitative results can be obtained using any vital staining technique, including for example lissamine green staining, rose Bengal staining, and/or sodium fluorescein staining. Such staining techniques can be used to identify and/or quantify a degree of epithelial cellular disruption, for example by staining dead and degenerate cells while not staining healthy cells. Treated patients/subjects may also exhibit improved keratitis scores.

Example 3: Pilot Study

Background:

Conventional treatments for dry eye syndrome have focused on addressing tear levels and inflammation, but have failed to demonstrate efficacy in all patients. New therapies have increasingly addressed meibomian gland dysfunction (MGD). Topical spironolactone is a drug with low toxicity and the potential to regulate and improve sebaceous gland meibum secretions through a variety of mechanisms.

Purpose:

The objective of this study was to investigate the effectiveness of topical spironolactone in treating MGD, a major component of dry eye syndrome.

Design:

Retrospective cohort study.

Methods Setting: Clinical Practice.

Patient Study Population: Twenty patients from November 2014 to February 2015 with moderate to severe meibomian gland disease were included in this study. The prescribing information included administering a composition to both eyes of the subjects 4 times per day as a topical drop for one month and then 2 times per day henceforth for maintenance. Any formulation in this disclosure can be administered according to any protocol provided herein as well, or according to typical treatment protocols. Patients who were taking glaucoma medications, steroid eye drops and other lipid-altering eye drops prior to starting spironolactone were excluded. Several parameters were analyzed in describing MGD, including subjective global dry eye assessment, keratitis and conjunctival staining, anterior blepharitis grade, gland obstruction grade, meibum turbidity grade, meibum viscosity grade, zone A posterior lid margin grade, best corrected vision, and Schirmer's score. These parameters were compared in a pre-post study. Follow-up times ranged from 1 to 7 weeks, with an average of approximately 3 weeks.

Main Outcome Measures:

Parameters in the prevalence of meibomian gland dysfunction (subjective global assessment, lissamine green keratitis and conjunctival staining, anterior blepharitis grade, obstruction grade, vascularity grade, turbidity grade, zone A grade, vision and Schirmer's tear score) in patients with moderate to severe MGD.

Results:

Patients with moderate to severe MGD had improved self-reported global assessment scores (p=0.010), turbidity score (p=0.001), and Zone A scores (p=0.025) after treatment with topical ophthalmic suspensions of spironolactone.

Conclusions:

MGD patients reported improved dry eye symptoms after using compounded topical spironolactone ophthalmic suspensions for longer than one week. The quality of expressed meibum secretions of MGD patients clinically showed improved clarity and viscosity post-treatment. Inflammation decreased at the avascular region 0.5 mm posterior to the posterior lid margin post-treatment. This study demonstrates the potential for spironolactone to regulate meibum quality and address inflammation in treating MGD.

Spironolactone has potential to be used to treat MGD due to its pharmacological properties. It is believed that spironolactone addresses oil production in MGD by modulating testosterone receptors, and address inflammation associated with MGD by suppressing production of cytokines and cortisol. Patients taking spironolactone had an improvement in subjective dry-eye symptoms, turbidity scores (quality of expressed meibum), and Zone A scores (posterior lid margin inflammation).

Detailed Methods:

This study is a retrospective chart review of 20 patients, 12 female and 8 male with a mean age of 48.3±18.4 years. Corrected visual acuity was measured prior to starting spironolactone and during the follow-up visit. Corrected visual acuity was recorded in log MAR based on the corresponding line read correctly on the Snellen chart. Patients self-assessed dry-eye global scores based on the presence of symptoms during the current exam on a scale from 0 to 10 based on (0=no dry eye symptoms, 10=the worst dry eye symptoms felt ever). Keratitis and conjunctival scores were evaluated using lissamine green staining on nasal conjunctival, central corneal, and temporal conjunctival regions on a scale from 0 to 3 (0=no staining and 3=confluent staining). Schirmer's test was performed without topical anesthetics to evaluate tear film production. Anterior blepharitis scores were evaluated using a slit lamp and graded on a scale from 0 to 4 (0=no dandruff and 4=dandruff across the entire lash line). Lid margin abnormalities such as vascularity and inflammation of the avascular region 0.5 mm posterior to the posterior lid margin (Zone A) were evaluated and graded on a scale from 0 to 4 (0=no vascularization and 4=vascularization of the entire margin). See Arita, R., Zavala, M., & Yee, R. W., "MGD Diagnosis," Curr Opthalmol Rep, 49-57 (Jun. 4, 2014). Meibomian gland expression (obstruction) was evaluated by applying pressure to the lower lid and graded on a scale from 0 to 4. The quality of the expressed meibum (turbidity and viscosity) was also evaluated and graded from 0 to 4 (0=clear oil; 4=cloudy & toothpaste-like). The diagnosis of MGD was made based on the presence of a score of 3+ on symptoms or 2+ on lid margin abnormalities (see Arita et al., "Proposed diagnostic criteria for obstructive meibomian gland dysfunction," Ophthalmology, 116:2058-2063 (2009)). Patients taking glaucoma medications or steroid eye-drops were excluded from the study. Patients included in the study started using spironolactone eye drops prior to using other topical eye medications or systemic medications to treat any dry eye conditions. Patients were prescribed spironolactone after previously taking omega-3 fatty acid and flax seed oil supplements and practicing blinking exercises with limited improvement. The average follow-up interval in this pre-post study was 22.4 days, ranging from 2 to 6 weeks. Statistical analysis was performed using STATA 13 by fitting scored data to a non-parametric model with the Wilcoxon signed-rank test and testing continuous data with a paired t-test.

Detailed Results:

The mean subjective global assessment score of MGD prior to treatment based on self-reported symptoms was 6.0±0.610. After treatment with spironolactone, the mean subjective global assessment score was 4.6±0.534. The patients had an improvement of 1.4±0.597 (p=0.0113) in self-reported global assessment scores. The mean keratitis and conjunctival staining scores of the right eye prior to treatment were 1.0±0.201, 0.10±0.100, and 0.78±0.194 in the nasal, corneal, and temporal regions respectively. The mean keratitis and conjunctival staining scores of the left eye prior to treatment were 0.95±0.198, 0.20±0.138, and 0.30±0.164 in the nasal, corneal, and temporal regions respectively. Post-treatment mean keratitis and conjunctival scores were 0.83±0.189, 0.050±0.050 and 0.55±0.181, in nasal, corneal, and temporal regions of the right eye and 0.60±0.148, 0.20±0.156 and 0.40±0.134 in nasal, corneal, and temporal regions of the left eye, respectively. The mean change of keratitis and conjunctival scores were −0.20±0.142 (p=0.168), −0.05±0.114 (p=0.655), and −0.23±0.187 (p=0.293) in nasal, corneal, and temporal regions of the right eye and −0.35±0.146 (p=0.037), 0.00±0.126 (p=1.00), 0.10±0.204 (p=0.366) in nasal, corneal, and temporal regions of the left eye.

The mean visions of patients prior to treatment were 0.072±0.036 and 0.022±0.034 log Mar units in the left and right eyes, respectively. After treatment, the vision of patients was 0.063±0.032 and 0.069±0.051 log units in the left and right eyes, respectively. The mean change in MAR was −0.0088±0.032 log units (p=0.999) for the left eye and 0.047±0.043 log units (p=0.236) for the right eye.

The mean Schirmer's scores of patients prior to treatment were 14.15±2.171 mm and 14.30±2.306 mm for the left and right eyes, respectively. Post treatment, the mean Shirmir scores were 13.63±2.421 mm and 14.55±2.426 mm for the left and right eyes. The mean change in Schirmer's score was 0.250±1.008 and −0.525±1.496 for the left and right eyes, respectively.

The mean anterior blepharitis score was 0.55±0.226 prior to treatment and 0.38±0.114 post-treatment; mean improvement in anterior blepharitis score was 0.175±0.230 (p=0.8985). The mean vascularity score was 1.73±0.264 prior to treatment and 1.48±0.253 post-treatment, with a mean improvement of 0.25±0.194 (p=0.2699). The mean obstruction score was 1.98±0.234 prior to treatment and 1.58±0.236 post-treatment, with a mean improvement of 0.40±0.222 (p=0.1114). The mean turbidity score was 2.95±0.125 prior to treatment and 2.3±0.193 post-treatment, with a mean improvement of 0.65±0.141 (p=0.0010), corresponding to an improvement of 22.03%. The mean zone A score was 3.55±0.149 prior to treatment and 3.125±0.188 post-treatment, with a mean improvement of 0.425±0.186 (p=0.0248), corresponding to an improvement of 11.97%. The pre-treatment measurements, post-treatment measurements, and change between pre- and post-treatment are summarized below in Tables 1-3.

TABLE 1

Pre-treatment Descriptive Statistics

| Parameter | Mean | Standard Deviation |
|---|---|---|
| Subjective Global Assessment | 6.0 | 2.73 |
| Conjunctival OD (Nasal) | 1.0 | 0.896 |
| Keratitis OD (Corneal) | 0.10 | 0.447 |
| Conjunctival OD (Temporal) | 0.78 | 0.866 |
| Conjunctival OS (Nasal) | 0.95 | 0.887 |
| Keratitis OS (Corneal) | 0.20 | 0.616 |
| Conjunctival OS (Temporal) | 0.30 | 0.733 |
| Vision OD (log Mar units) *n = 19 | 0.022 | 0.149 |
| Vision OS (log Mar units) | 0.072 | 0.160 |
| Schirmer's OD (mm) | 14.2 | 9.71 |
| Schirmer's OS (mm) | 14.3 | 10.3 |
| Anterior Blepharitis | 0.55 | 1.01 |
| Vascularity | 1.73 | 1.18 |
| Obstruction | 1.98 | 1.04 |
| Turbidity | 2.95 | 0.560 |
| Zone A | 3.55 | 0.667 |

*One patient was excluded from vision since he had prosthesis in his right eye

TABLE 2

Post-treatment Descriptive Statistics

| Parameter | Mean | Standard Deviation |
|---|---|---|
| Subjective Global Assessment | 4.6 | 2.39 |
| Conjunctival OD (Nasal) | 0.83 | 0.847 |
| Keratitis OD (Corneal) | 0.050 | 0.224 |
| Conjunctival OD (Temporal) | 0.55 | 0.809 |
| Conjunctival OS (Nasal) | 0.60 | 0.661 |
| Keratitis OS (Corneal) | 0.20 | 0.696 |
| Conjunctival OS (Temporal) | 0.40 | 0.598 |
| Vision OD (log Mar units) *n = 19 | 0.069 | 0.221 |
| Vision OS (log Mar units) | 0.063 | 0.141 |
| Schirmer's OD (mm) | 13.6 | 10.8 |
| Schirmer's OS (mm) | 14.6 | 10.9 |
| Anterior Blepharitis | 0.38 | 0.510 |
| Vascularity | 1.48 | 1.13 |
| Obstruction | 1.58 | 1.05 |
| Turbidity | 2.3 | 0.865 |
| Zone A | 3.125 | 0.841 |

*One patient was excluded from vision since he had prosthesis in his right eye

TABLE 3

Pre-post change

| Parameter | Mean Change | Change % | SEM | p-value |
|---|---|---|---|---|
| Subjective Global Assessment | −1.4 | −23.33% | 2.67 | 0.0113 |
| Conjunctival OD (Nasal) | −0.20 | −20.00% | 0.637 | 0.168 |
| Keratitis OD (Corneal) | −0.05 | −50.00% | 0.510 | 0.655 |
| Conjunctival OD (Temporal) | −0.23 | −29.49% | 0.835 | 0.293 |
| Conjunctival OS (Nasal) | −0.35 | −36.84% | 0.651 | 0.037 |
| Keratitis OS (Corneal) | 0.00 | 0.00% | 0.562 | 1.00 |
| Conjunctival OS (Temporal) | 0.10 | 20.00% | 0.912 | 0.366 |
| Vision OD (log Mar units) *n = 19 | 0.047 | 213.64% | 0.189 | 0.236 |
| Vision OS (log Mar units) | 0.009 | −7.20% | 0.144 | 0.999 |
| Schirmer's OD (mm) | −0.525 | −3.71% | 6.69 | 0.7295 |
| Schirmer's OS (mm) | 0.25 | 1.75% | 4.51 | 0.8067 |
| Anterior Blepharitis | −0.175 | −31.82% | 1.03 | 0.8985 |
| Vascularity | −0.25 | −14.45% | 0.866 | 0.2699 |
| Obstruction | −0.4 | −20.25% | 0.995 | 0.1114 |
| Turbidity | −0.65 | −22.03% | 0.630 | 0.0010 |
| Zone A | −0.425 | −11.97% | 0.832 | 0.0248 |

*One patient was excluded from vision since he had prosthesis in his right eye

Figure 1B:
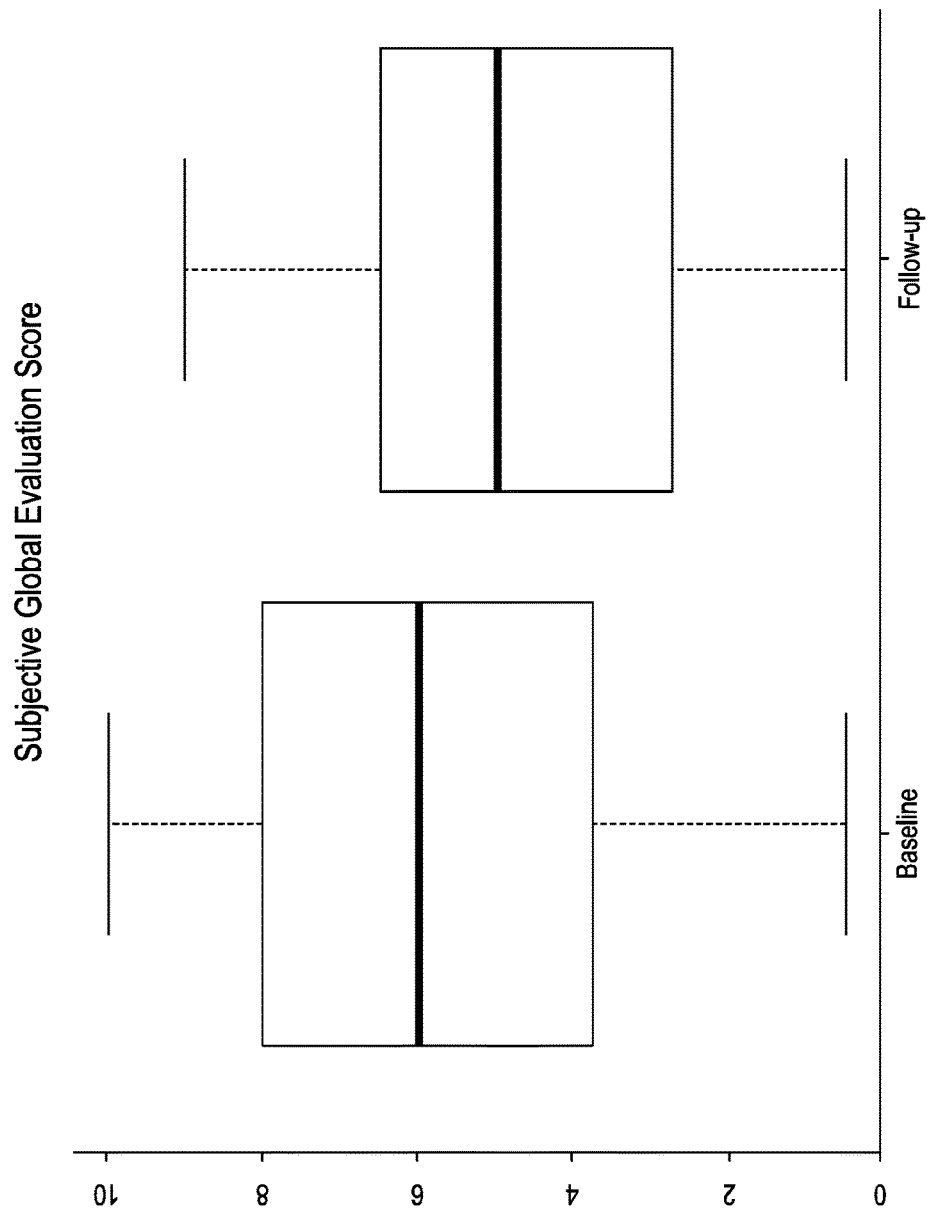
FIG. 1B is a box plot of baseline and follow-up Subjective Global Assessment Scores of the Pilot Study of Example 3.
Figure 2A:
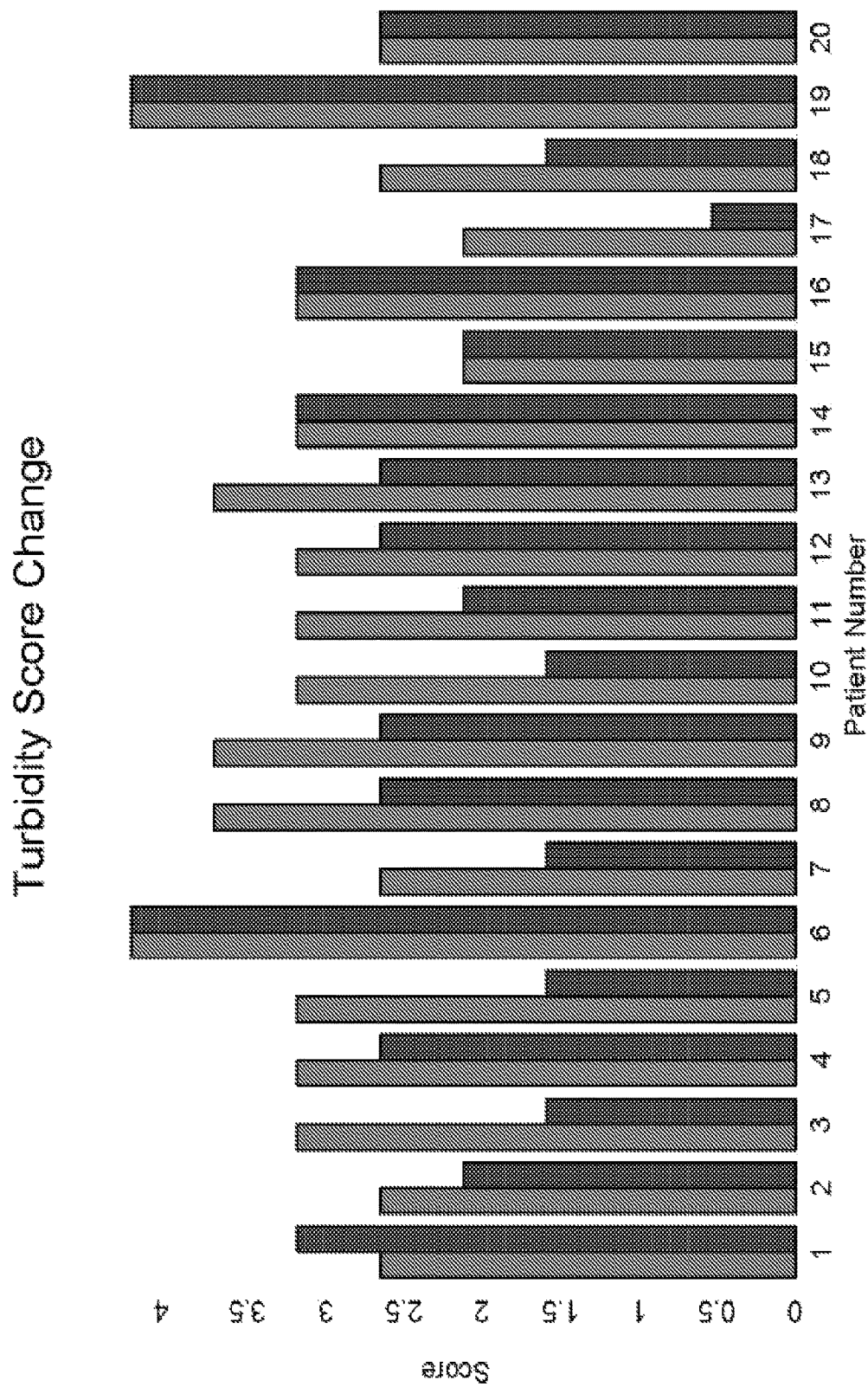
FIG. 2A is a bar graph showing baseline and follow-up Turbidity Scores for individual patients of the Pilot Study of Example 3.
Figure 2B:
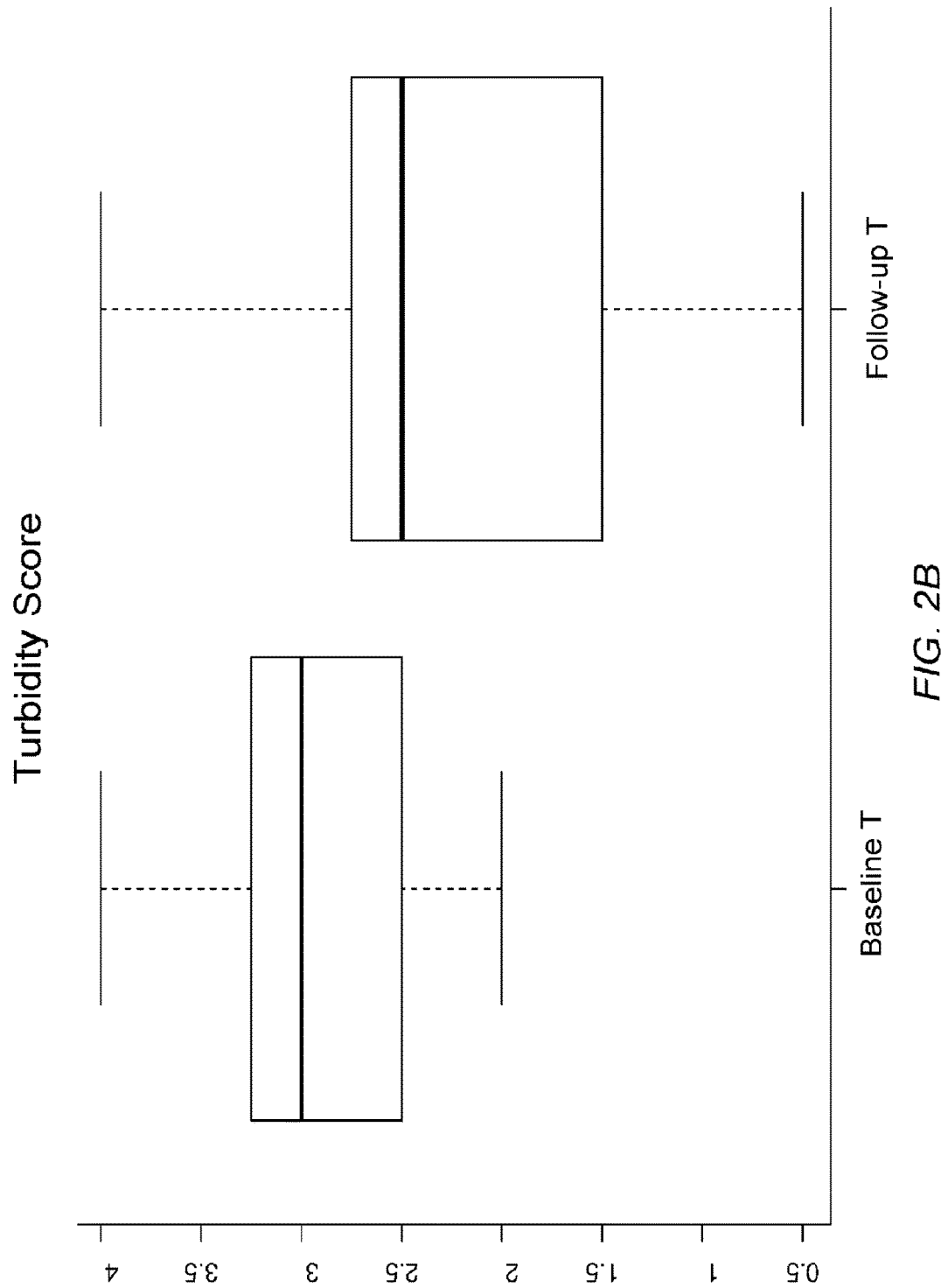
FIG. 2B is a box plot of baseline and follow-up Turbidity Scores of the Pilot Study of Example 3.
Figure 3A:
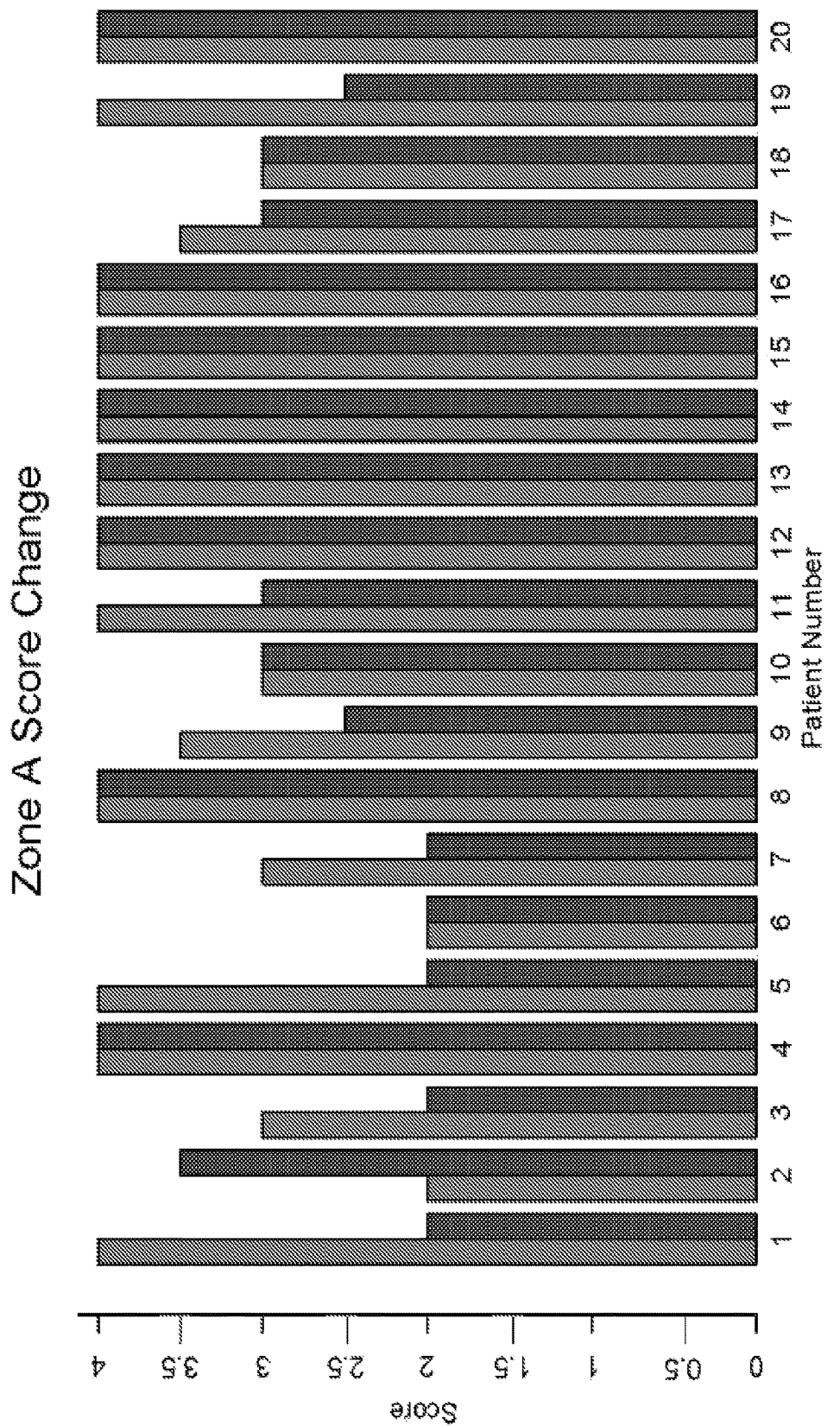
FIG. 3A is a bar graph showing baseline and follow-up Zone A Scores for individual patients of the Pilot Study of Example 3.
Figure 3B:
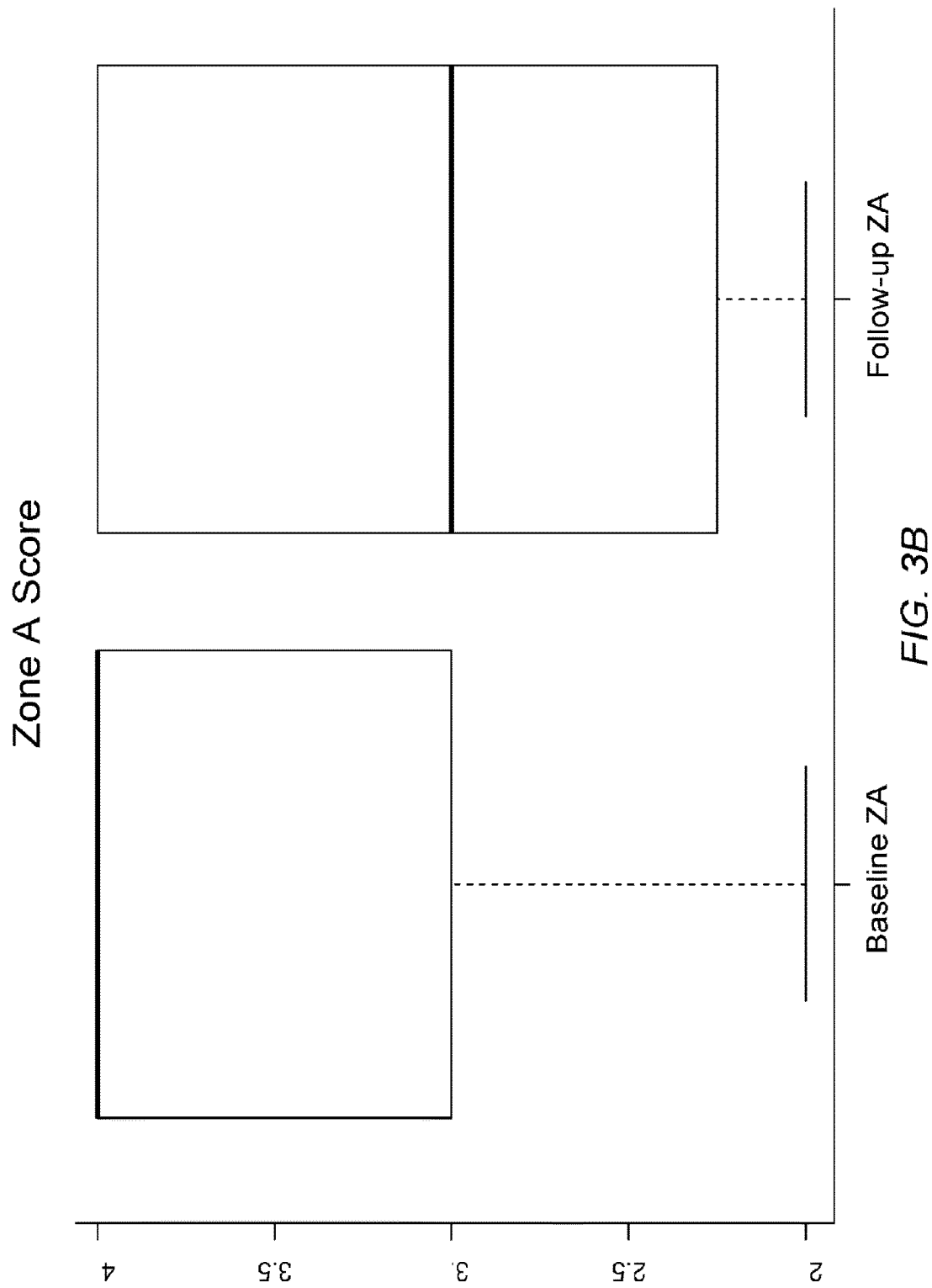
FIG. 3B is a box plot of baseline and follow-up Zone A Scores of the Pilot Study of Example 3.

The change in statistically significant measurements (global evaluation, turbidity, and zone A) is plotted in FIGS. 1A-3B. As noted, the majority of the parameters measured showed trends of improvement.

Discussion:

This study is the first to evaluate the potential of topical spironolactone to treat MGD. This study is expected to be published in 2016 as "Topical Spironolactone in the Treatment of Meibomian Gland Dysfunction," by Brian S. Wong, Mikhail de Jesus, Richard W. Yee. Based on the results shown in Table 3, application of a topical spironolactone ophthalmic suspension has a statistically significant effect (p<0.05) on the subjective global assessment score, keratitis and conjunctival score in the nasal region of the right eye, turbidity grade, and the zone A grade. The change in global evaluation score (p=0.0113) suggests that patients' symptoms associated with dry eye syndrome (redness, swelling, irritation) decreased. The most statistically significant change is in the turbidity grade (p=0.0010). This change suggests that spironolactone may have a role in changing the quality of the expressed meibum through various mechanisms based on its diverse pharmacological properties.

Moreover, change in zone A grade (p=0.0248) may reflect the anti-inflammatory properties of spironolactone.

Spironolactone was first used as a potassium-sparing diuretic due to its antagonistic activity at aldosterone receptors. Many other properties of spironolactone have been discovered including its dual activity at testosterone receptors (see Térouanne, et al., "A stable prostatic bioluminescent cell line to investigate androgen and antiandrogen effects," Molecular and Cellular Endocrinology, 160 (1-2): 39-49, (2001)). Due to this property, spironolactone has been used off-label for the treatment of hormonal acne in women and to suppress unwanted effects of androgens in individuals undergoing gender reassignment. Since testosterone has a known role in the development and function of meibomian glands, it is reasonable to assume that spironolactone may have additional off-label uses and may benefit patients with MGD.

The presence of MGD in patients with low testosterone levels was identified in 2002 and subsequent studies have confirmed the influence of androgens on gene regulation in meibomian glands (see Sullivan, et al., "Androgen deficiency, Meibomian gland dysfunction, and Evaporative dry eye," *Ann N Y Acad Sci.*, 966:211-222, (2002)). A study in 2011, showed that levels of testosterone were elevated in patients with MGD and suggested that elevated levels of testosterone should be used as a diagnostic criteria for diagnosing MGD (see Sahin, et al., "Meibomian Gland Dysfunction: Endocrine Aspects," *ISRN Ophthalmology*, vol. 2011, Article ID 465198, 6 pages, (2011)). After an improvement in the understanding of MGD, one explanation of these conflicting results is that Sullivan was studying hyposecretory states resulting in MGD, while Sahin was studying hypersecretory states resulting in MGD. This suggests that it is necessary to have a proper balance of testosterone levels for meibomian glands to secrete meibum with an optimal quality for maintaining tear film. Spironolactone's property as a weak partial agonist of testosterone may help maintain a balanced level of testosterone. This property of spironolactone may address the underlying cause of MGD pathogenesis in addition to addressing the symptoms that may be associated with its anti-inflammatory properties.

An advantage of using topical spironolactone, rather than oral spironolactone, is that a lower concentration is necessary to deliver an effective dose directly to the site of action. Topical use of spironolactone still has possible side effects. A small percentage of the patients reported a mild temporary burning sensation in the eye after administration of spironolactone. The role of the anti-aldosterone activity of spironolactone in the eye is unclear. The presence of a renin-angiotensin system has been identified as a potential target for lowering intraocular pressure in patients with glaucoma. Strain and Chaturvedi, "The renin-angiotensin-aldosterone system and the eye in diabetes," *J Renin Angiotensin Aldosterone Syst.*, 3:243-246, 2002.

Example 4: Administering Dapsone and Spironolactone to a Subject

In many patients, dapsone and spironolactone, when administered topically in conjunction with one another, results in an additive effect (i.e. 10% to 30% improvement) in subjective complaints of surface symptoms and objective findings of overall improved inflammation based on vascularity, zone A scores and bulbar and palpebral injection. Dapsone and spironolactone can be administered simultaneously, sequentially, in the same or different compositions. There may or may not be improvement of the keratitis seen with surface disease depending on the severity of the aqueous components and how much morbidity that has occurred with essential macro and micro components of the ocular surface anatomy. Dapsone, however, may be contraindicated in patients with a well-documented sulfa allergy.

An exemplary 15 mL ophthalmic solution composition comprising 3 mg spironolactone and 2.5 mg dapsone per mL can be prepared as follows. Dissolve about 0.31 grams spironolactone and about 0.26 grams dapsone in an alcohol. Ethyl alcohol can be used from 70-95% ethyl alcohol, such as from 80-90%, or 85-95%. Return solution to syringe for filtering into a sterile glass mortar in a clean room. Approximately 8 mL of ethyl alcohol is needed for each 0.3 grams of spironolactone powder. Prepare an extra 1 mL syringe comprising an alcohol, such as from 70-95% ethyl alcohol. Using a filter, such as a 0.1, 0.2, 0.3, 0.4, 0.5 micron Teflon filter, filter the solution into a sterile glass mortar and rinse the filter with the extra alcohol (e.g., from 1-5 mL extra alcohol) to remove any spironolactone left in the filter. Place 1 mL of alcohol into the filtered solution and allow the alcohol to evaporate (typically several hours, to overnight) to leave a sterile powder in the glass mortar. Draw up 30 mL spironolactone vehicle (such as hypromellose 0.01% to 5%, such as from 0.05% to 0.8%, or from 0.1% to 0.5%, or from 0.2% to 1%, or from 0.3% to 2%, or from 0.4% to 3%, or from 0.5% to 4%, or 5%, with or without NaCl (i.e., preservative free, PF)) (see also Example 5 below for exemplary vehicle) using a 30 mL syringe from a sterile Pyrex bottle. In the same glass mortar, add drop by drop from 10 mL, to 20 mL, to 30 mL, to 40 mL, to 50 mL of spironolactone vehicle or spironolactone-PF vehicle up to the desired concentration, stirring/grinding vigorously. For a composition comprising about 2.5 mg dapsone and 3 mg spironolactone per mL, the amount of vehicle added is around 90-100 mL, such as about 91, 92, 93, 94, 95, 96, 97, 98, 99, or 100 mL. Continue to stir/grind well to make a paste, then a suspension. In the same sterile Pyrex bottle, add the syringe of the suspension and let spin, for example for up to 1, 2, 3, 4, 5, 6, 7, 8, 9, or 10 hours. Final pH of the composition is in the range of a pH of about 4-8, such as a pH of 4, 4.5, 5, 5.5, 6, 6.5, 7, 7.5, or 8. Transfer contents of pyrex bottle into an appropriate sized droptainer, for example, a 15 mL droptainer.

Example 5: Exemplary Aldosterone Antagonist Vehicle

An ophthalmic vehicle for administering aldosterone antagonist, such as spironolactone, can be prepared by the following method. Heat about 80-100 mL of water for irrigation in a beaker until steaming, about 70-120 degrees Celsius, such as about 70-110 degrees Celsius, or from about 75-115 degrees Celsius, or from about 80-105 degrees Celsius. Add about 0.04-0.06 grams (such as 0.0.045, 0.05, 0.055, 0.06 grams) edetate disodium dihydrate; about 0.4-0.6 grams (such as 0.45, 0.48, 0.50, 0.52, 0.55, 0.57, 0.59, 0.6 grams) dibasic sodium phosphate; about 0.05-0.2 grams (such as 0.06, 0.08, 0.10, 0.12, 0.14, 0.16, 0.18, or 0.2 grams) monobasic sodium phosphate; and about 0.5-3 grams (such as 0.8, 1, 1.2, 1.4, 1.7, 2, 2.2, 2.5, 2.8, or 3 grams) potassium chloride and stir until dissolved. Add about 0.05-0.8 grams (such as 0.08, 0.1, 0.15, 0.2, 0.25, 0.3, 0.35, 0.4, 0.5, 0.6, 0.7, or 0.8 grams) methocel to the heated solution and stir until clear. Bring to proper volume with water for irrigation. Add citric acid to adjust to desired acidic pH of about 4, 4.5, 5, 5.5, 6, 6.5, such as by using from 0.1-0.5 grams (such as 0.15, 0.2, 0.25, 0.3, 0.35, 0.4, 0.45, or 0.5 grams) citric acid. Transfer solution to an amber pyrex bottle. Close cap. Autoclave the solution until the solution reaches a temperature ranging from about 110 degrees Celsius to 130 degrees Celsius, such as up to 110, 111, 112, 113, 114, 115, 116, 117, 118, 119, 120, 121, 122, 123, 124 degrees Celsius and so on. Pressure can be in the range of 5-30 PSI, such as from 5-25 PSI, or from 10-20 PSI, or from 15-25 PSI, and so on. The residence time in the autoclave can range from about 20 minutes to 2 hours, such as from 30, 40, 45, 50, 55, 60, 75, 80, 90, 100, 110, or 120 minutes. The suspension can be stirred while autoclaving and/or cooling. Transfer the solution to a droptainer, such as a 10 mL, 15 mL, 20 mL, or 30 mL droptainer as appropriate. Final pH of the composition is in the range of a pH of about 4-8, such as a pH of 4, 4.5, 5, 5.5, 6, 6.5, 7, 7.5, or 8.

It will be understood that the Specification and Examples are illustrative of the present embodiments and that other embodiments within the spirit and scope of the claimed embodiments will suggest themselves to those skilled in the art. Although this disclosure has been described in connection with specific forms and embodiments thereof, it would be appreciated that various modifications other than those discussed above may be resorted to without departing from the spirit or scope of the embodiments as defined in the appended claims. For example, equivalents may be substituted for those specifically described, and in certain cases, particular applications of steps may be reversed or interposed all without departing from the spirit or scope for the disclosed embodiments as described in the appended claims. Additionally, one skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features.

It is noted in particular that where a range of values is provided in this specification, each value between the upper and lower limits of that range is also specifically disclosed. The upper and lower limits of these smaller ranges may independently be included or excluded in the range as well. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method for reducing or preventing one or more signs, symptoms, causes or effects of dry eye or meibomian gland dysfunction comprising:
   administering to an ocular region of a subject a composition comprising at least one aldosterone antagonist, or isomer, salt, or solvate thereof, one or more chelating agents, and a pharmaceutically acceptable carrier for reducing or preventing one or more signs, symptoms, causes or effects of dry eye or meibomian gland dysfunction.

2. The method of claim 1, wherein the at least one aldosterone antagonist, isomer, salt, or solvate thereof is selected from one or more compounds of Formula (I):

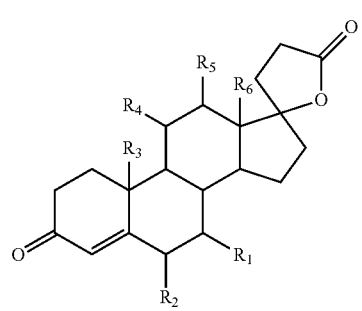

wherein $R_1$, $R_2$, $R_3$, $R_4$, $R_5$, and $R_6$ may each independently represent a hydrogen atom, an oxygen atom, a halogen atom, a saturated or unsaturated, branched or unbranched, substituted or unsubstituted aliphatic or aromatic hydrocarbon containing between 1 and 20 carbon atoms, an alkyl group, an alkenyl group, an alkynyl group, an alkoxy group, an acyl group, an acetyl group, an aryl group, an aryloxy group, an acrylyl group, a carbonyl group, a cycloalkyl group, a hydroxyalkyl group, an alkoxyalkyl group, a hydroxycarbonyl group, an alkoxycarbonyl group, an acyloxyalkyl group, a heteroaryl group, a heterocyclyl group, a ketal group, an acetal group, an amine group, an amide group, an imide group, an azide group, a sulfur-containing group, a thiol group, a sulfide group, a disulfide group, a sulfinyl group, a sulfonyl group, an acetylthio group, a formyl group, a furyl group, a hydroxyl group, a hetero atom, a cyano group, or an ester, ether, ketone, or aldehyde functional group, as well as substituted groups; and
wherein when $R_1$ and $R_2$ are each a hydrogen atom, there is a C—C double bond present between the carbon atoms to which $R_1$ and $R_2$ are attached.

3. The method of claim 2, wherein the aldosterone antagonist is spironolactone.

4. The method of claim 1, wherein the pharmaceutically acceptable carrier is a solution, a suspension, or an emulsion.

5. The method of claim 1, wherein the pharmaceutically acceptable carrier is chosen from water, an aqueous solution, a polymer or a nonionic surfactant.

6. The method of claim 5, wherein the polymer is hydroxypropyl methylcellulose, or the nonionic surfactant is a poloxamer.

7. The method of claim 1, wherein the composition is in the form of a liquid, a suspension, an emulsion, a gel, an ointment, a nanosized drug particle, a pellet, a slurry, an injectable, a solid, or a powder.

8. The method of claim 6, wherein the poloxamer is a pluronic poloxamer.

9. The method of claim 8, wherein the pluronic poloxamer is provided by pluronic lecithin organogel.

10. The method of claim 1, wherein the total amount of aldosterone antagonists is between 0.0005% to 1%, based on weight or volume of the composition, or between 0.005 mg/mL to 10 mg/mL.

11. The method of claim 1, wherein the ocular region is selected from a cornea, epithelial cells, goblet cells, tear film, ocular lymphatics, sclera, uvea, conjunctiva, lacrimal sac, lacrimal canals, lacrimal ducts, canthus, eyelids, eyelid glands, glands of Zeiss, glands of Wolfring, meibomian glands and its cellular and tissue components, and combinations thereof.

12. The method of claim 1, wherein the composition further comprises one or more antibiotics, steroids, anti-inflammation agents, analgesics, surfactants, buffering agents, pH adjusting agents, adjuvants, protein-based materials, and combinations thereof.

13. The method of claim 1, wherein the composition is applied for up to a total of 1-8 applications per day and according to the following schedule:
(i) for an indefinite period; and/or
(ii) from between 1-8 times daily; or
(iii) from between 1-4 times daily, for 1-4 weeks; or
(iv) from between 1-4 times daily, for up to 4 weeks, then from 1-2 times daily.

14. The method of claim 1, wherein the one or more signs, symptoms, causes or effects are chosen from impaired vision, burning sensation, redness, irritation, grittiness, filminess, inflammation, discomfort, pain, chemosis, chalasis, engorged vasculature, anterior lid margin vascularization, zone A posterior lid margin vascularization, eyelid disorders, swelling, lipids, vital staining, Schirmer's score, or meibomian gland obstruction, secretion, viscosity, secretion turbidity, loss, drop out, or dysfunction.

15. The method of claim 1, wherein the composition is a liquid and is administered as an ophthalmic drop to the ocular region of a subject.

16. A composition comprising from 0.0005% to 1%, based on weight or volume of the composition, or between 0.005 mg/mL to 10 mg/mL of one or more aldosterone antagonist, or isomer, salt, or solvate thereof and one or more chelating agents, in suspension, solution or emulsion in water, an aqueous solution, a polymer or a nonionic surfactant as a carrier.

17. The composition of claim 16, comprising from 0.0005% to 0.005%, based on weight or volume of the composition, or between 0.005 mg/mL to 0.05 mg/mL spironolactone as the aldosterone antagonist, or isomer, salt, or solvate thereof.

18. A composition comprising from 0.0005% to 1%, based on weight or volume of the composition, or between 0.005 mg/mL to 10 mg/mL, of one or more aldosterone antagonist, or isomer, salt, or solvate thereof in suspension, solution or emulsion, further comprising a sulfone antibiotic.

19. The composition of claim 18, wherein the sulfone antibiotic is dapsone.

20. The composition of claim 16, wherein the one or more aldosterone antagonist, or isomer, salt, or solvate thereof is chosen from one or more compounds of Formula (I):

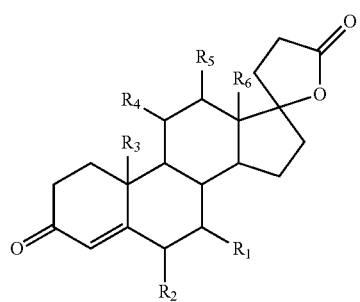

(I)

wherein $R_1$, $R_2$, $R_3$, $R_4$, $R_5$, and $R_6$ may each independently represent a hydrogen atom, an oxygen atom, a halogen atom, a saturated or unsaturated, branched or unbranched, substituted or unsubstituted aliphatic or aromatic hydrocarbon containing between 1 and 20 carbon atoms, an alkyl group, an alkenyl group, an alkynyl group, an alkoxy group, an acyl group, an acetyl group, an aryl group, an aryloxy group, an acrylyl group, a carbonyl group, a cycloalkyl group, a hydroxyalkyl group, an alkoxyalkyl group, a hydroxycarbonyl group, an alkoxycarbonyl group, an acyloxyalkyl group, a heteroaryl group, a heterocyclyl group, a ketal group, an acetal group, an amine group, an amide group, an imide group, an azide group, a sulfur-containing group, a thiol group, a sulfide group, a disulfide group, a sulfinyl group, a sulfonyl group, an acetylthio group, a formyl group, a furyl group, a hydroxyl group, a hetero atom, a cyano group, or an ester, ether, ketone, or aldehyde functional group, as well as substituted groups; and
wherein when $R_1$ and $R_2$ are each a hydrogen atom, there is a C—C double bond present between the carbon atoms to which $R_1$ and $R_2$ are attached.

21. The composition of claim 16, further comprising one or more antibiotics, steroids, anti-inflammation agents, analgesics, surfactants, buffering agents, pH adjusting agents, adjuvants, and combinations thereof.

22. The composition of claim 16, wherein spironolactone is present as the aldosterone antagonist, or isomer, salt, or solvate thereof in the composition.

23. A composition comprising from 0.0005% to 1%, based on weight or volume of the composition, or between 0.005 mg/mL to 10 mg/mL, of one or more aldosterone antagonist, or isomer, salt, or solvate thereof, in suspension, solution or emulsion, in a polymer or a nonionic surfactant as a carrier,
further comprising one or more antibiotic present in the composition in an amount ranging from 0.005% to 4%, based on weight or volume of the composition, or from 0.05 mg/mL to 40 mg/mL.

24. The composition of claim 19, wherein the dapsone is present in the composition in an amount ranging from 0.005% to 4%, based on weight or volume of the composition, or from 0.05 mg/mL to 40 mg/mL.

25. A composition comprising from 0.0005% to 1%, based on weight or volume of the composition, or between 0.005 mg/mL to 10 mg/mL of one or more aldosterone antagonist, or isomer, salt, or solvate thereof in suspension, solution or emulsion in a polymer or a nonionic surfactant as a carrier,
wherein the carrier is a hydroxypropyl methylcellulose carrier and comprises from about 0.01 wt % to 5 wt % hydroxypropyl methylcellulose.

26. A composition comprising from 0.0005% to 1%, based on weight or volume of the composition, or between 0.005 mg/mL to 10 mg/mL of one or more aldosterone antagonist, or isomer, salt, or solvate thereof in suspension, solution or emulsion in a polymer or a nonionic surfactant as a carrier,
wherein the nonionic surfactant is a poloxamer.

27. The composition of claim 26, wherein the poloxamer is a pluronic poloxamer.

28. The composition of claim 27, wherein the pluronic poloxamer is provided by pluronic lecithin organogel.

29. The method of claim 2, wherein the at least one aldosterone antagonist, isomer, salt or solvate thereof is chosen from spironolactone, eplerenone, canrenone, prorenone, mexrenone, isomers, salts, and solvates thereof, and combinations thereof.

30. The composition of claim 20, wherein the one or more aldosterone antagonist, isomer, salt, or solvate thereof is chosen from one or more of spironolactone, eplerenone, canrenone, prorenone, mexrenone, isomers, salts, and solvates thereof, and combinations thereof.

31. An ophthalmic composition comprising:
   spironolactone, an isomer, salt or solvate thereof,
   with one or more chelating agent in a pharmaceutically acceptable carrier,
   provided in the form of a solution, suspension, or emulsion based eye drop.

32. The method of claim 1, wherein the amount of the at least one aldosterone antagonist, or isomer, salt, or solvate thereof is between 0.0005% to 0.005%, based on weight or volume of the composition, or between 0.005 mg/mL up to 0.05 mg/mL.

33. The method of claim 32, wherein the at least one aldosterone antagonist is spironolactone.

34. The method of claim 1, wherein the one or more chelating agents are chosen from edetate salts.

35. The method of claim 34, wherein the edetate salts are chosen from edetate disodium, edetate calcium disodium, edetate sodium, edetate trisodium, and/or edetate dipotassium.

36. The composition of claim 16, wherein the one or more chelating agents are chosen from edetate salts.

37. The composition of claim 36, wherein the edetate salts are chosen from edetate disodium, edetate calcium disodium, edetate sodium, edetate trisodium, and/or edetate dipotassium.

38. The method of claim 33, wherein the one or more chelating agents are chosen from edetate salts.

39. The method of claim 38, wherein the edetate salts are chosen from edetate disodium, edetate calcium disodium, edetate sodium, edetate trisodium, and/or edetate dipotassium.

40. The method of claim 2 wherein the halogen atom is chosen from fluorine, chlorine, bromine and iodine.

41. The method of claim 20 wherein the halogen atom is chosen from fluorine, chlorine, bromine and iodine.

* * * * *